United States Patent
Reeves et al.

(10) Patent No.: US 6,387,495 B1
(45) Date of Patent: May 14, 2002

(54) SUPERABSORBENT-CONTAINING COMPOSITES

(75) Inventors: William G. Reeves, Appleton; Emmanuelle C. Damay; Wendy L. Hamilton, both of Neenah; Patsy A. Hansen, Omro, all of WI (US); Jack N. Lindon, Alpharetta, GA (US); Heather A. Sorebo, Appleton, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 0 days.

(21) Appl. No.: 09/545,156

(22) Filed: Apr. 7, 2000

Related U.S. Application Data

(60) Provisional application No. 60/129,744, filed on Apr. 16, 1999.

(51) Int. Cl.[7] ............................. A61F 13/15; B32B 5/16
(52) U.S. Cl. ....................... 428/402; 428/403; 428/404; 428/405; 604/358; 604/367; 604/368; 604/372; 604/374
(58) Field of Search ................. 428/402, 403, 428/404, 405; 604/358, 367, 368, 372, 374

(56) References Cited

U.S. PATENT DOCUMENTS

| | | | |
|---|---|---|---|
| 3,089,824 A | 5/1963 | Wurster | 424/489 |
| 3,117,027 A | 1/1964 | Lindlof et al. | 118/303 |
| 3,196,827 A | 7/1965 | Wurster et al. | 118/24 |
| 3,241,520 A | 3/1966 | Wurster et al. | 118/62 |
| 3,253,944 A | 5/1966 | Wurster | 427/213 |
| 3,395,708 A | 8/1968 | Hervey et al. | 604/375 |
| 3,532,097 A | 10/1970 | Jones, Sr. | 604/366 |
| 3,554,862 A | 1/1971 | Hervey et al. | 162/158 |
| 3,585,998 A | 6/1971 | Hayford | 604/359 |
| 3,670,731 A | 6/1972 | Harmon | 604/368 |
| 3,677,886 A | 7/1972 | Forssblad et al. | 162/72 |
| 3,871,376 A | 3/1975 | Kozak | 604/291 |
| 3,901,236 A * | 8/1975 | Assarsson | 604/368 |
| 3,932,322 A | 1/1976 | Duchane | 524/430 |
| 3,932,687 A | 1/1976 | Okamoto et al. | 442/334 |
| 3,935,363 A | 1/1976 | Burkholder et al. | 442/118 |
| 3,972,855 A | 8/1976 | Martinsson et al. | 558/38 |
| 4,055,184 A | 10/1977 | Karami | 604/359 |
| 4,073,732 A | 2/1978 | Lauer et al. | 210/491 |
| 4,115,277 A | 9/1978 | Swank | 210/436 |
| 4,143,163 A | 3/1979 | Hutchison et al. | 426/96 |
| 4,144,122 A | 3/1979 | Emanuelsson et al. | 162/158 |

(List continued on next page.)

FOREIGN PATENT DOCUMENTS

| | | |
|---|---|---|
| EP | 0 132 128 A1 | 1/1985 |
| EP | 0 483 730 A1 | 5/1992 |
| EP | 0 489 967 A1 | 6/1992 |
| EP | 0 499 672 A1 | 8/1992 |
| EP | 0 278 601 B2 | 11/1992 |

(List continued on next page.)

OTHER PUBLICATIONS

Derwent World Patent Database abstract of JP 08–322,863 A: Description of Shigeru KK; Wacoal Co. Ltd., "Pad For Adjusting Body Shape."

American Society for Testing Materials (ASTM) Designation: D 1921–89, "Standard Test Methods for Particle Size (Sieve Analysis of Plastic Materials," pp. 493–496, published Aug. 1989.

(List continued on next page.)

*Primary Examiner*—Leszek Kiliman
(74) *Attorney, Agent, or Firm*—Thomas M. Parker

(57) ABSTRACT

Superabsorbent-containing composites containing at least one particle of a superabsorbent material covered with at least a first layer of at least one particle of at least one coating material. The superabsorbent materials are desirably stiff-gelling superabsorbent materials. The superabsorbent-containing composites of the present invention are particularly suitable for use in sanitary napkins, diapers and other disposable absorbent articles that handle complex fluids.

50 Claims, 14 Drawing Sheets

U.S. PATENT DOCUMENTS

| | | | |
|---|---|---|---|
| 4,272,514 A | 6/1981 | Spence | 424/69 |
| 4,303,471 A | 12/1981 | Laursen | 162/158 |
| 4,327,728 A | 5/1982 | Elias | 604/368 |
| 4,335,722 A | 6/1982 | Jackson | 604/364 |
| 4,351,699 A | 9/1982 | Osborn, III | 162/112 |
| 4,381,782 A | 5/1983 | Mazurak et al. | 604/368 |
| 4,381,783 A | 5/1983 | Elias | 640/368 |
| 4,381,784 A | 5/1983 | Aberson et al. | 640/368 |
| 4,432,833 A | 2/1984 | Breese | 162/158 |
| 4,433,972 A | 2/1984 | Malfitano | 604/385.01 |
| 4,476,323 A | 10/1984 | Hellsten et al. | 564/294 |
| 4,482,429 A | 11/1984 | Klowak | 162/111 |
| 4,500,670 A | 2/1985 | McKinley et al. | 524/445 |
| 4,551,331 A | 11/1985 | Rudin | 424/738 |
| 4,643,727 A | 2/1987 | Rosenbaum | 604/369 |
| 4,654,161 A | 3/1987 | Kollmeier et al. | 424/70.12 |
| 4,668,564 A | 5/1987 | Orchard | 442/226 |
| 4,676,784 A | 6/1987 | Erdman et al. | 604/368 |
| 4,693,713 A | 9/1987 | Chmelir et al. | 604/368 |
| 4,717,498 A | 1/1988 | Maxon | 556/428 |
| 4,734,478 A | 3/1988 | Tsubakimoto et al. | 527/300 |
| 4,824,681 A | 4/1989 | Schobel et al. | 426/5 |
| 4,824,901 A | 4/1989 | Alexander et al. | 524/555 |
| RE32,957 E | 6/1989 | Elias | 604/368 |
| 4,840,692 A | 6/1989 | Kamstrup-Larsen | 156/252 |
| 4,846,176 A | 7/1989 | Golden | 607/104 |
| 4,883,478 A | 11/1989 | Lerailler et al. | 604/360 |
| 4,909,243 A | 3/1990 | Frank et al. | 602/58 |
| 4,960,845 A | 10/1990 | O'Lenick, Jr. | 528/25 |
| 5,002,814 A | 3/1991 | Knack et al. | 428/85 |
| 5,015,334 A | 5/1991 | Derrick | 162/168.1 |
| 5,070,168 A | 12/1991 | O'Lenick, Jr. | 528/10 |
| 5,070,171 A | 12/1991 | O'Lenick, Jr. | 528/33 |
| 5,073,619 A | 12/1991 | O'Lenick, Jr. | 528/26 |
| 5,087,506 A | 2/1992 | Palumbo | 428/194 |
| 5,098,979 A | 3/1992 | O'Lenick, Jr. | 528/15 |
| 5,120,812 A | 6/1992 | O'Lenick, Jr. et al. | 528/25 |
| 5,122,544 A | 6/1992 | Bailey et al. | 521/40.5 |
| 5,135,294 A | 8/1992 | Ohshima et al. | 312/319.1 |
| 5,149,335 A | 9/1992 | Kellenberger et al. | 604/372 |
| 5,149,765 A | 9/1992 | O'Lenick, Jr. | 528/25 |
| 5,196,499 A | 3/1993 | O'Lenick, Jr. | 528/15 |
| 5,197,959 A | 3/1993 | Buell | 604/385.23 |
| 5,230,959 A * | 7/1993 | Young | 428/372 |
| 5,236,594 A | 8/1993 | O'Reilly et al. | 210/656 |
| 5,237,035 A | 8/1993 | O'Lenick, Jr. et al. | 528/27 |
| 5,280,099 A | 1/1994 | Imperante et al. | 528/28 |
| 5,283,123 A | 2/1994 | Carter et al. | 428/403 |
| 5,296,434 A | 3/1994 | Karl et al. | 502/117 |
| 5,300,055 A | 4/1994 | Buell | 604/385.23 |
| 5,300,666 A | 4/1994 | Imperante et al. | 556/428 |
| 5,330,457 A | 7/1994 | Cohen | 604/378 |
| 5,336,208 A | 8/1994 | Rosenbluth et al. | 604/329 |
| 4,500,670 C1 | 12/1994 | McKinley et al. | 524/445 |
| 5,419,956 A | 5/1995 | Roe | 442/294 |
| 5,429,633 A | 7/1995 | Davis et al. | 604/387 |
| 5,436,066 A | 7/1995 | Chen | 442/398 |
| 5,486,569 A | 1/1996 | Henderson et al. | 525/116 |
| 5,489,469 A | 2/1996 | Kobayashi et al. | 442/393 |
| 4,217,901 C1 | 6/1996 | Bradstreet et al. | 604/368 |
| 5,527,902 A | 6/1996 | Loth et al. | 536/57 |
| 5,587,239 A | 12/1996 | Ueba et al. | 428/362 |
| 5,593,399 A | 1/1997 | Tanzer et al. | 604/368 |
| 5,603,946 A | 2/1997 | Constantine | 424/445 |
| H1639 H | 3/1997 | Crainic | |
| 5,609,588 A | 3/1997 | DiPalma et al. | 604/369 |
| 5,633,316 A | 5/1997 | Gartner et al. | 525/54.32 |
| 5,637,165 A | 6/1997 | Chen | 156/62.2 |
| 5,681,579 A | 10/1997 | Freeman | 424/448 |
| 5,697,961 A | 12/1997 | Kiamil | 607/108 |
| 5,713,881 A * | 2/1998 | Rezoi et al. | 604/368 |
| 5,147,343 C1 | 3/1998 | Kellenberger | 604/368 |
| 5,728,082 A | 3/1998 | Gustafsson et al. | 604/368 |
| 5,728,742 A | 3/1998 | Staples et al. | 521/57 |
| 5,731,365 A | 3/1998 | Engelhardt et al. | 523/206 |
| 5,800,417 A | 9/1998 | Goerg-Wood et al. | 604/367 |
| 5,800,418 A | 9/1998 | Ahr | 604/368 |
| 5,814,567 A | 9/1998 | Yahiaoui et al. | 442/118 |
| 5,830,496 A | 11/1998 | Freeman | 424/445 |
| 5,847,089 A | 12/1998 | Damodaran et al. | 516/103 |
| 5,855,571 A * | 1/1999 | Steger | 604/368 |
| 5,883,231 A | 3/1999 | Achter et al. | 530/362 |

FOREIGN PATENT DOCUMENTS

| | | |
|---|---|---|
| EP | 0 339 461 B1 | 1/1993 |
| EP | 0 697 217 A1 | 2/1996 |
| EP | 0 532 002 B1 | 5/1997 |
| EP | 0 779 065 A2 | 6/1997 |
| FR | 2 627 080 A1 | 8/1989 |
| FR | 2 628 761 A1 | 9/1989 |
| GB | 2 211 418 B | 1/1992 |
| WO | WO 98/06364 A1 | 2/1998 |
| WO | WO 98/13003 A1 | 4/1998 |
| WO | WO 98/14152 A1 | 4/1998 |
| WO | WO 98/14155 A1 | 4/1998 |
| WO | WO 98/43684 A1 | 10/1998 |
| WO | WO 98/48857 A1 | 11/1998 |

OTHER PUBLICATIONS

Hiemenz, Paul C., *Principles of Colloid and Surface Chemistry*, Marcel Dekker, Inc., 1977, Chapter 2, pp. 42–83 and Chapter 5, pp. 160–208.

Lichstein, Bernard M., "Demand Wettability, A New Method For Measuring Absorbency Characteristics of Fabrics," *INDA Technical Symposium—Nonwoven Product Technology*, Washington, D.C., Mar. 1974, pp. 129–142.

O'Lenick Jr., Anthony J. et al., "Silicone Compounds: Not Just Oil Phases Anymore," *Soap/Cosmetics/Chemical Specialties*, Jun. 1998, pp. 55–57.

* cited by examiner

US 6,387,495 B1

SUPERABSORBENT-CONTAINING COMPOSITES

This Application claims benefit of Prov. No. 60/129,744 filed Apr. 16, 1999.

BACKGROUND

The present invention relates to superabsorbent-containing composites having an improved efficacy in the handling of a complex fluid. More particularly, the present invention relates to superabsorbent-containing composites capable of selectively removing at least a portion of an amount of at least one specific component of a complex fluid.

Superabsorbent materials possess a number of attributes that make them attractive in many different applications. As a result of their superior water-absorbing attributes, superabsorbent materials have supplanted much of the traditional absorbents in disposable diapers and have made significant improvements in the performance of disposable feminine hygiene products and disposable adult incontinence products. The basic property of water absorption has suggested the use of superabsorbent materials in many other applications, including paper towels, surgical sponges, meat trays, disposable mats for outside doorways and in bathrooms, and for household pet litter, bandages and wound dressings.

The largest use of superabsorbent materials, however, is in disposable personal hygiene products. These products include, in order of volume of superabsorbent material used, diapers, training pants, adult incontinence products and feminine hygiene products. Of these, diapers accounted for over 90% of the total superabsorbent material sold in 1995. Because of this, the development of superabsorbent properties in general has been focused on optimizing absorbency of urine.

A challenge for the developers of products into which superabsorbent materials are incorporated, however, is the very significant difference between the fluids to be absorbed by the various disposable absorbent products. With diapers, for example, the fluid is typically urine, a simple fluid of primarily water, salts and nitrogenous materials such as urea. With feminine hygiene products, for example, the fluid is typically menses, a complex fluid including water, salts, and cells. In such complex fluids, the cells are far too large to diffuse into the network structure of the superabsorbent material, and may instead adsorb onto the surfaces of the particles of superabsorbent material. The high osmotic pressure of partially swollen superabsorbent material can de-water the cells if they are in direct contact and this can lead to a nearly impermeable surface layer of cells surrounding the superabsorbent material, resulting in a severe reduction in the efficacy of the superabsorbent material. These factors suggest that the nature of the superabsorbent material for absorbing complex fluids such as menses should be different from the superabsorbent material used for absorbing simple fluids such as urine. As a result of this suggestion, various approaches have been disclosed regarding the development of superabsorbent materials capable of absorbing complex fluids such as menses.

A number of these approaches disclose that superabsorbent material suitable for absorbing simple fluids may be chemically treated to enhance its ability to absorb complex fluids. While considered as being somewhat effective, these approaches at times provide for complicated methods of manufacture, which invariably increase the cost of the resulting superabsorbent material. In addition, it has been found that some of these approaches tend to increase the possibility of the user being exposed to harmful contaminants during use.

As an alternative to the foregoing chemical treatment of superabsorbent material, other approaches have focused on the development of superabsorbent materials specifically designed to absorb complex fluids. Unfortunately, any improvement in the ability of these specifically designed superabsorbent materials to absorb complex fluids is oftentimes offset by a diminishment in their ability to absorb simple fluids. Moreover, these specifically-designed superabsorbent materials are relatively expensive compared to the cost of mass-produced superabsorbent materials developed primarily for absorbing simple fluids such as urine.

SUMMARY

The present inventors have recognized the difficulties and problems inherent in the prior art and in response thereto conducted intensive research in developing superabsorbent-containing composites having an improved efficacy in the handling of complex fluids. Despite factors suggesting to the contrary, the present inventors surprisingly found that a mass-produced, readily obtainable and affordable superabsorbent material, developed primarily for absorbing simple fluids such as urine, can be incorporated into a superabsorbent-containing composite capable of selectively removing at least a portion of an amount of at least one specific component of a complex fluid. Due to the use of mass-produced, readily obtainable superabsorbent materials in a relatively uncomplicated process of manufacture, the superabsorbent-containing composites of the present invention are relatively in expensive when compared to the cost of superabsorbent materials specifically designed to absorb complex fluids. While demonstrating an improved efficacy in the handling of complex fluids, the superabsorbent-containing composites of the present invention surprisingly do not demonstrate any significant diminishment in ability to absorb simple fluids. In addition, the superabsorbent-containing composites of the present invention do not expose the user to harmful contaminants during use.

In one embodiment of the present invention, a superabsorbent-containing composite includes at least one particle of a stiff-gelling superabsorbent material covered with at least a first layer of at least one particle of at least one coating material. The first layer of the coating material is in intimate association with and covering the surface of the superabsorbent material. The superabsorbent material is capable of selectively removing at least a portion of an amount of at least one specific component of a complex fluid. The coating material is also capable of selectively removing at least a portion of an amount of at least one specific component of a complex fluid. The intimate association of the coating material with the superabsorbent material is achieved with the use of an association agent.

In another embodiment of the present invention, a superabsorbent-containing composite has at least one particle of a stiff-gelling superabsorbent material covered with at least a first layer of at least one particle of at least one coating material. The first layer of the coating material is in intimate association with and covering the surface of the superabsorbent material. The superabsorbent material is capable of selectively removing at least a portion of an amount of at least one specific component of a complex fluid. The coating material is also capable of selectively removing at least a portion of an amount of at least one specific component of a complex fluid. The coating material in this embodiment is chemically modified. The intimate association of the coating material with the superabsorbent material is achieved with the use of an association agent.

In still another embodiment of the present invention, a superabsorbent-containing composite includes at least one particle of a stiff-gelling superabsorbent material covered with at least a first layer of at least one particle of at least one coating material. The first layer of the coating material is in intimate association with and covering the surface of the superabsorbent material. The superabsorbent material is capable of removing at least a portion of an amount of at least one specific component of a complex fluid. In this embodiment, the coating material substantially inhibits those components of a complex fluid having a diameter greater than about five microns from being adsorbed onto the surface of the superabsorbent material of the superabsorbent-containing composite.

DRAWINGS

The foregoing and other features, aspects and advantages of the present invention will become better understood with regard to the following description, appended claims and accompanying drawings where:

DESCRIPTION

Figure 1:
FIG. 1 is a photomicrograph, at an original magnification level of ×170, illustrating a superabsorbent-containing composite of the present invention. The superabsorbent material is Favor SXM 880 and the coating material is Avicel 101.
Figure 2:
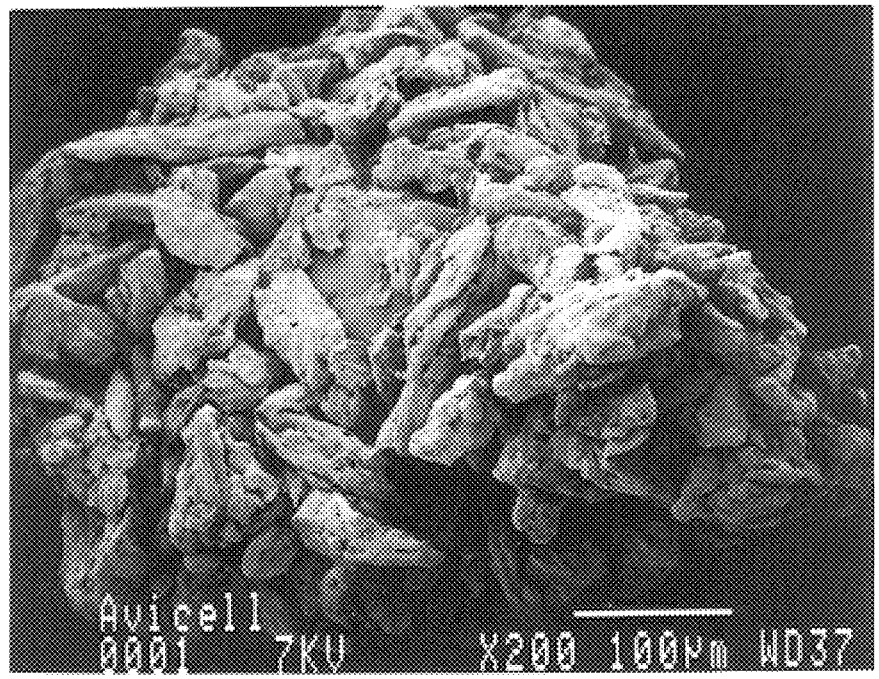
FIG. 2 is a photomicrograph, at an original magnification level of ×200, illustrating a superabsorbent-containing composite of the present invention. The superabsorbent material is Favor SXM 880 and the coating material is Avicel 101.
Figure 3:
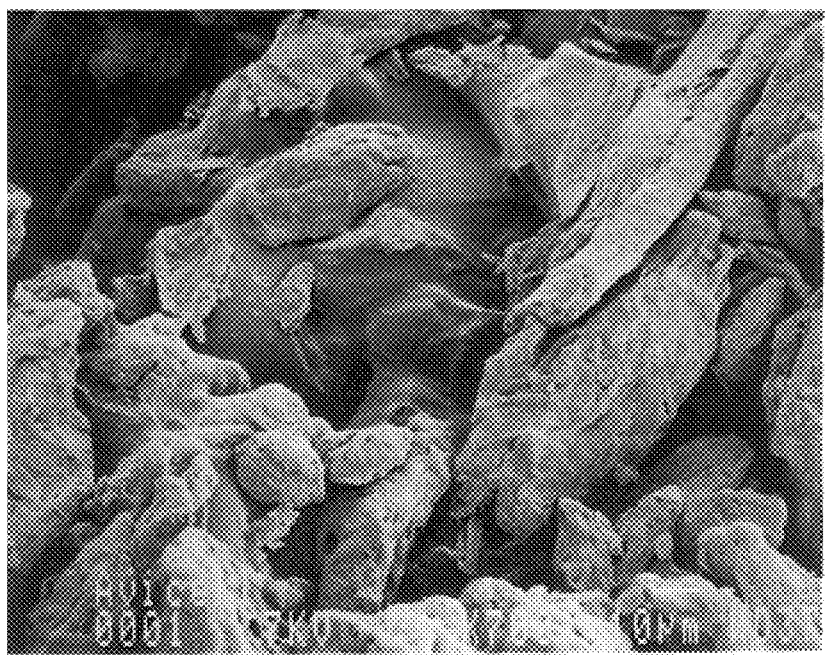
FIG. 3 is a photomicrograph, at an original magnification level of ×700, illustrating a superabsorbent-containing composite of the present invention. The superabsorbent material is Favor SXM 880 and the coating material is Avicel 101.
Figure 4:
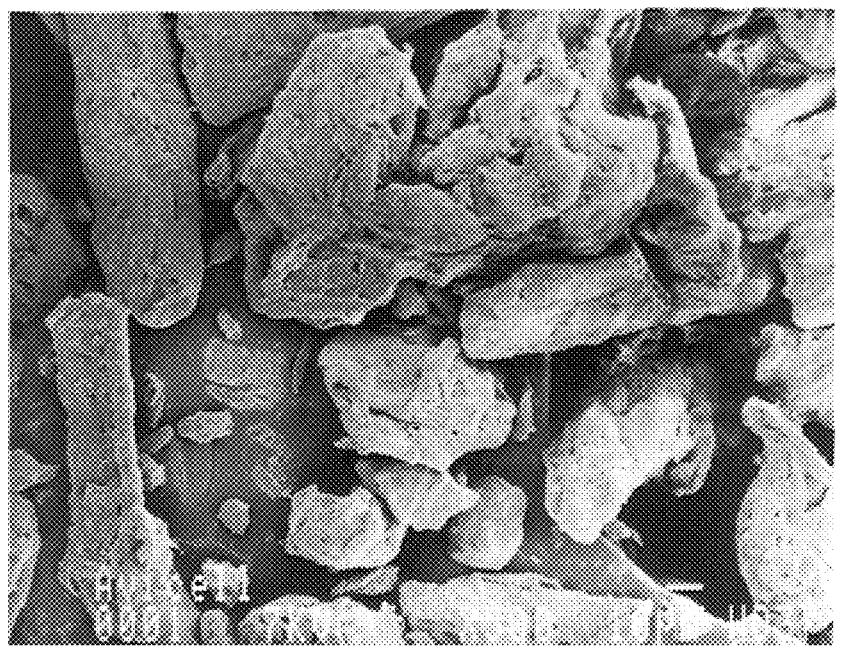
FIG. 4 is a photomicrograph, at an original magnification level of ×500, illustrating a superabsorbent-containing composite of the present invention. The superabsorbent material is Favor SXM 880 and the coating material is Avicel 101.
Figure 5:
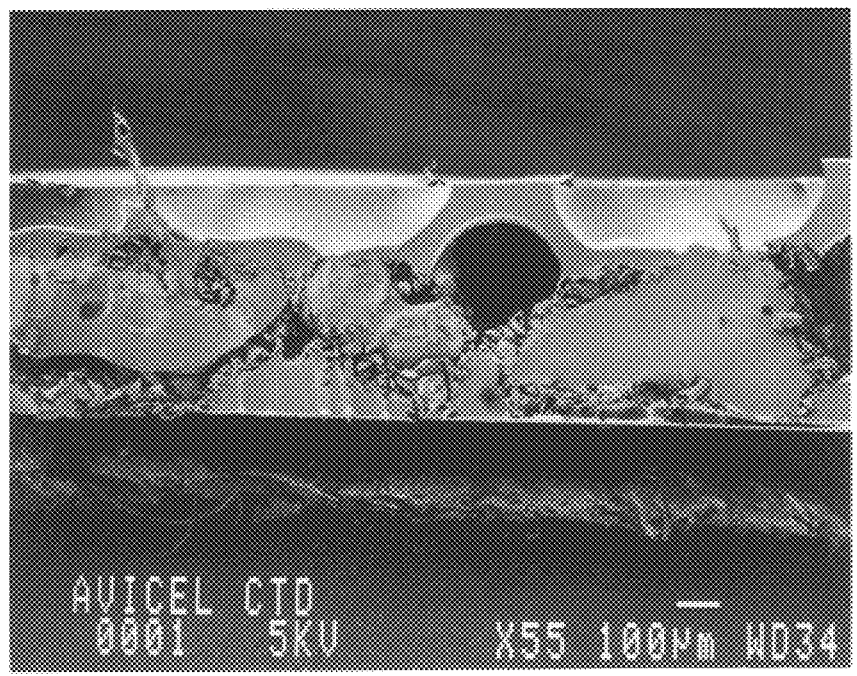
FIG. 5 is a photomicrograph, at an original magnification level of ×55, illustrating a cross-section of superabsorbent-containing composites of the present invention. The superabsorbent material is Favor SXM 880 and the coating material is Avicel 101.
Figure 6:
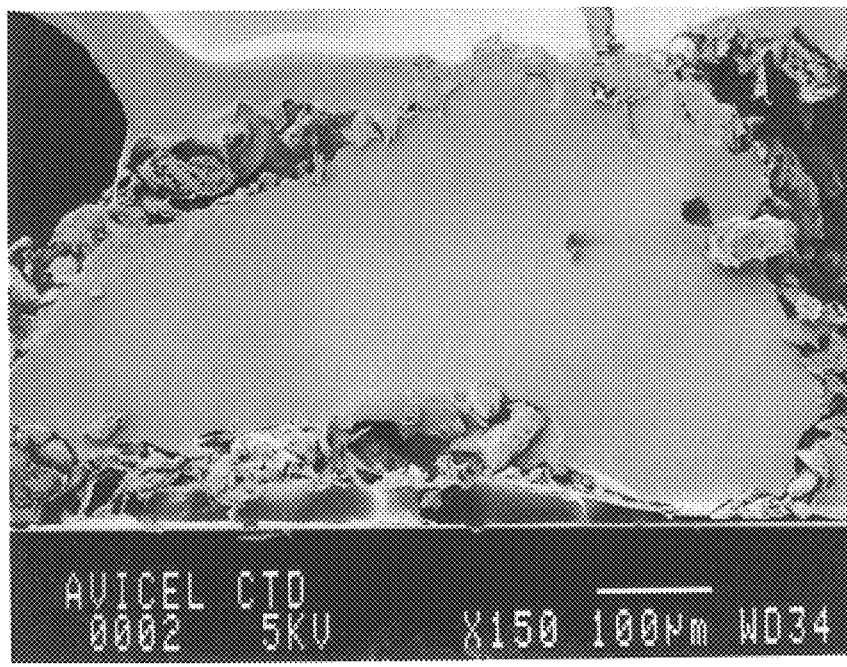
FIG. 6 is a photomicrograph, at an original magnification level of ×150, illustrating a cross-section of a superabsorbent-containing composite of the present invention. The superabsorbent material is Favor SXM 880 and the coating material is Avicel 101.
Figure 7:
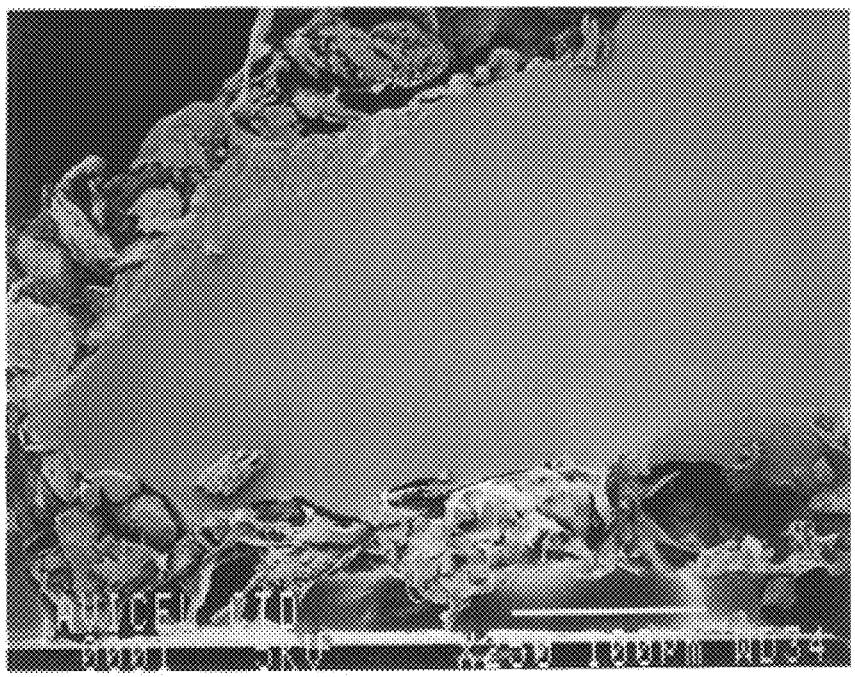
FIG. 7 is a photomicrograph, at an original magnification level of ×250, illustrating a cross-section of a superabsorbent-containing composite of the present invention. The superabsorbent material is Favor SXM 880 and the coating material is Avicel 101.
Figure 8:
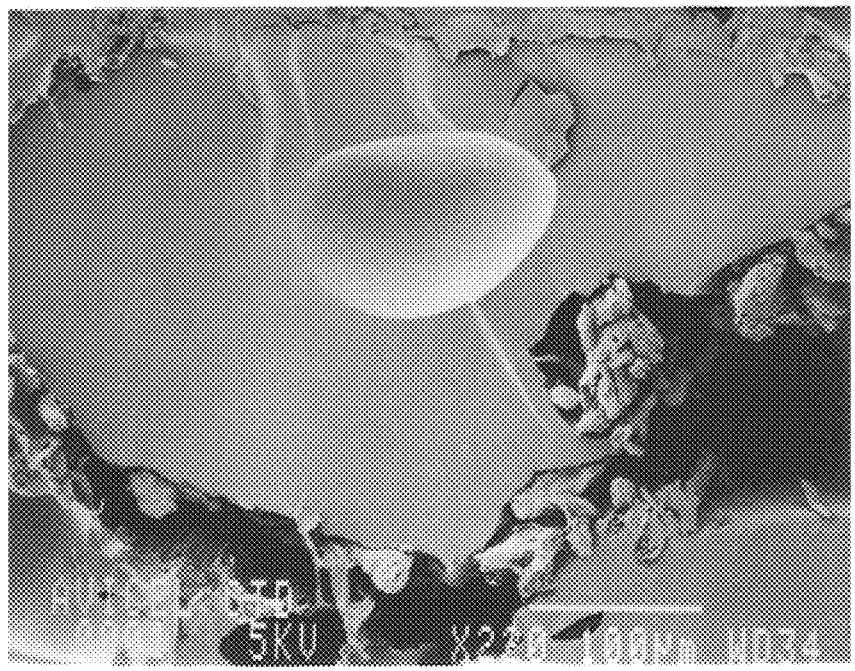
FIG. 8 is a photomicrograph, at an original magnification level of ×220, illustrating a cross-section of a superabsorbent-containing composite of the present invention. The superabsorbent material is Favor SXM 880 and the coating material is Avicel 101.
Figure 9:
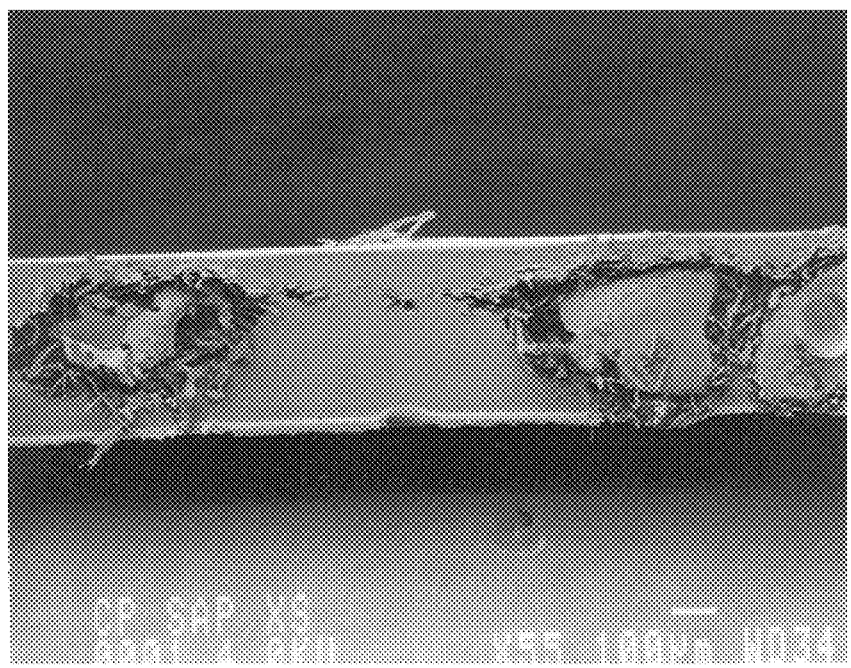
FIG. 9 is a photomicrograph, at an original magnification level of ×55, illustrating a cross-section of superabsorbent-containing composites of the present invention. The superabsorbent material is Favor SXM 880 and the coating material is EXCEL 110, a commercially available cellulose powder.
Figure 10:
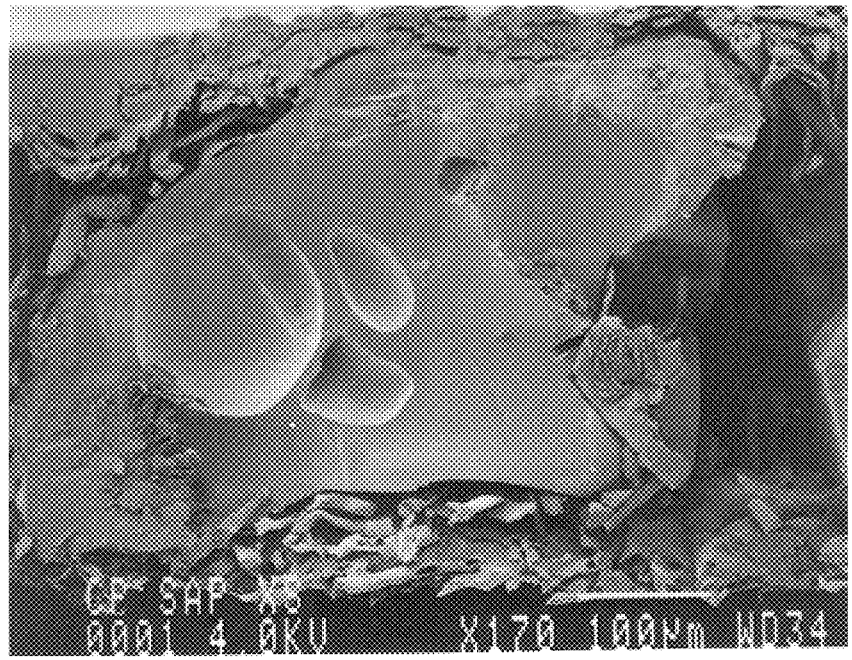
FIG. 10 is a photomicrograph, at an original magnification level of ×170, illustrating a cross-section of a superabsorbent-containing composite of the present invention. The superabsorbent material is Favor SXM 880 and the coating material is EXCEL 110, a commercially available cellulose powder.
Figure 11:
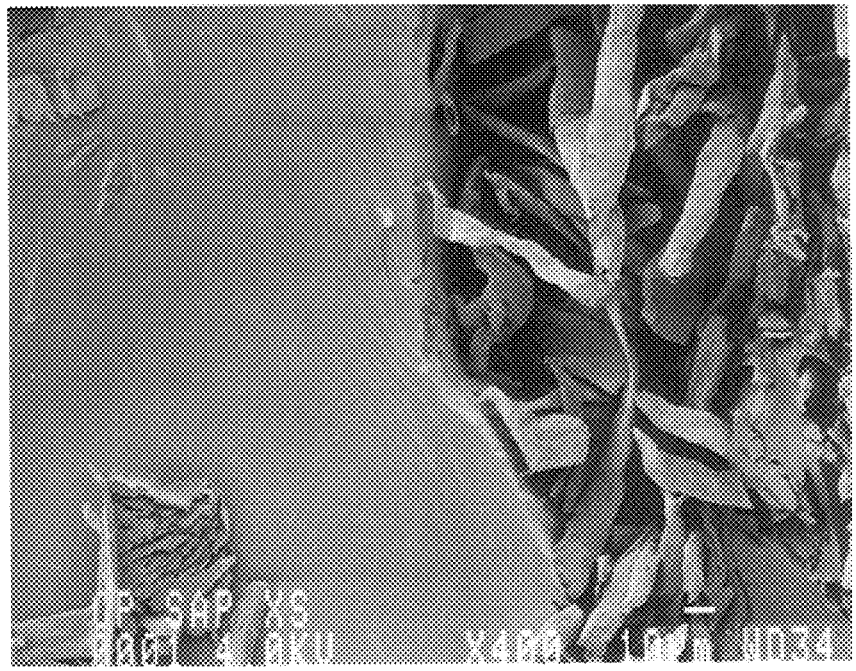
FIG. 11 is a photomicrograph, at an original magnification level of ×400, illustrating a cross-section of a superabsorbent-containing composite of the present invention. The superabsorbent material is Favor SXM 880 and the coating material is EXCEL 110, a commercially available cellulose powder.
Figure 12:
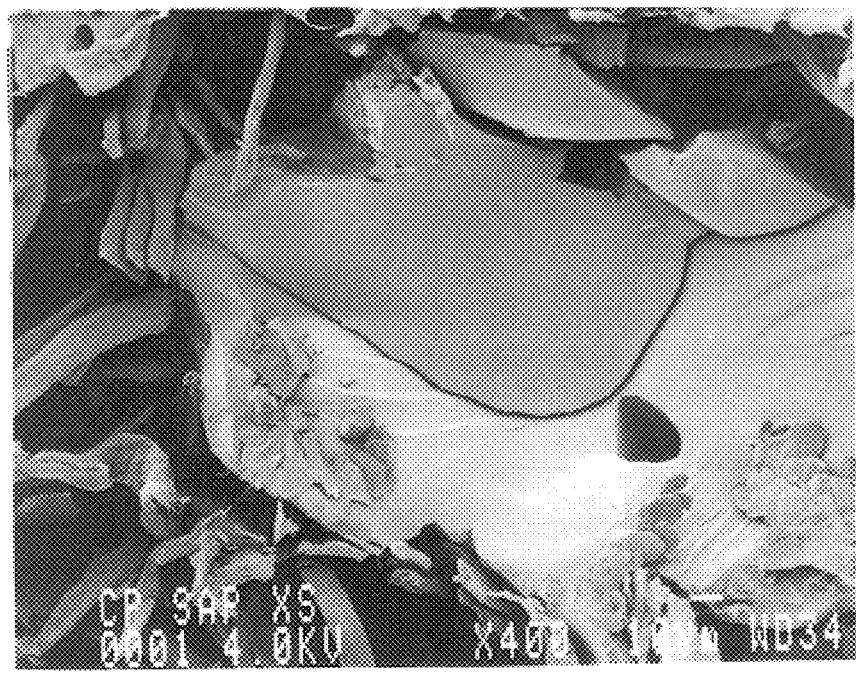
FIG. 12 is a photomicrograph, at an original magnification level of ×400, illustrating a cross-section of superabsorbent-containing composites of the present invention. The superabsorbent material is Favor SXM 880 and the coating material is EXCEL 110, a commercially available cellulose powder.

The superabsorbent-containing composites of the present invention include at least one particle of superabsorbent material covered with at least one particle of coating material.

By "particle," "particles," "particulate," "particulates" and the like, it is meant that a material is generally in the form of discrete units. The particles can include granules, pulverulents, powders or spheres. Thus, the particles can have any desired shape such as, for example, cubic, rod-like, polyhedral, spherical or semi-spherical, rounded or semi-rounded, angular, irregular, etc. Shapes having a large greatest dimension/smallest dimension ratio, like needles, flakes and fibers, are also contemplated for use herein. The use of "particle" or "particulate" may also describe an agglomeration including more than one particle, particulate or the like.

As used herein, the phrase "intimate association" and other similar terms are intended to encompass configurations including the following: those where at least a portion of the surface of at least one particle of a layer of coating material is in contact with a portion of the surface of at least one particle of superabsorbent material; and/or those where at least a portion of the surface of at least one particle of a layer of coating material is in contact with a portion of the surface of at least one other particle of a layer of coating material.

As used herein, the phrase "complex fluid" describes a fluid generally characterized as being a viscoelastic mixture including specific components having generally inhomogeneous physical and/or chemical properties. It is the inhomogeneous properties of the specific components that challenge the efficacy of a superabsorbent material in the handling of complex fluids, such as, for example, blood, menses, loose passages, nasal discharges and the like. In contrast with complex fluids, simple fluids, such as, for example, urine, physiological saline, water and the like, are generally characterized as being Newtonian and including one or more components having generally homogeneous physical and/or chemical properties. As a result of having homogeneous properties, the one or more components of simple fluids behave substantially similarly during absorption or adsorption.

Although a complex fluid is generally characterized herein as including specific components having inhomogeneous properties, each specific component of a complex fluid generally has homogeneous properties. Consider for example a hypothetical complex fluid having three specific components: red blood cells, blood protein molecules and water molecules. Upon examination, one skilled in the art could easily distinguish between each of the three specific components according to their generally inhomogeneous properties. Moreover, when examining a particular specific component such as the red blood cell component, one skilled in the art could easily recognize the generally homogeneous properties of the red blood cells.

A wide variety of materials capable of selectively removing at least a portion of an amount of at least one specific component of a complex fluid can be suitably employed as the superabsorbent material of the present invention. It is desired, however, to employ superabsorbent materials in particle form capable of absorbing large quantities of fluids, such as water, and of retaining such absorbed fluids under moderate pressures. It is even more desired to use relatively inexpensive and readily obtainable superabsorbent materials that have typically been developed primarily to absorb simple fluids.

As used herein, "superabsorbent material," "superabsorbent materials" and the like are intended to refer to a water-swellable, water-insoluble organic or inorganic material capable, under the most favorable conditions, of absorbing at least about 10 times its weight and, preferably, at least about 15 times its weight in an aqueous solution containing 0.9 weight percent of sodium chloride. Such materials include, but are not limited to, hydrogel-forming polymers which are alkali metal salts of: poly(acrylic acid); poly(methacrylic acid); copolymers of acrylic and methacrylic acid with acrylamide, vinyl alcohol, acrylic esters, vinyl pyrrolidone, vinyl sulfonic acids, vinyl acetate, vinyl morpholinone and vinyl ethers; hydrolyzed acrylonitrile grafted starch; acrylic acid grafted starch; maleic anhydride copolymers with ethylene, isobutylene, styrene, and vinyl ethers; polysaccharides such as carboxymethyl starch, carboxymethyl cellulose, methyl cellulose, and hydroxypropyl cellulose; poly(acrylamides); poly(vinyl pyrrolidone); poly(vinyl morpholinone); poly(vinyl pyridine); and copolymers and mixtures of any of the above and the like. The hydrogel-forming polymers are preferably lightly cross-linked to render them substantially water-insoluble. Cross-linking may be achieved by irradiation or by covalent, ionic, van der Waals attractions, or hydrogen bonding interactions, for example. A desirable superabsorbent material is a lightly cross-linked hydrocolloid. Specifically, a more desirable superabsorbent material is a partially neutralized polyacrylate salt.

Superabsorbent materials employed in the present invention suitably should be able to absorb a liquid under an applied load. For purposes of this application, the ability of a superabsorbent material to absorb a liquid under an applied load and thereby perform work is quantified as the Absorbency Under Load (AUL) value. The AUL value is expressed as the amount (in grams) of an approximately 0.9 weight percent saline (sodium chloride) solution absorbed by about 0.160 grams of superabsorbent material when the superabsorbent material is under a load. Common loads, further described hereinbelow, include those of about 0.29 pound per square inch, 0.57 pound per square inch, and about 0.90 pound per square inch. Superabsorbent materials suitable for use herein desirably are stiff-gelling superabsorbent materials having an AUL value under a load of about 0.29 pound per square inch of at least about 7; alternatively, at least about 9; alternatively, at least about 15; alternatively, at least about 20; alternatively, at least about 24; and, finally, alternatively, at least about 27 g/g. (Although known to those skilled in the art, the gell stiffness or shear modulus of a superabsorbent material is further described in U.S. Pat. No. 5,147,343 and European Publication No. 0339461 B1, the disclosure of each of which is incorporated herein by reference to the extent that each is consistent (i.e., does not conflict) with the present specification.) Useful superabsorbent materials, generally developed primarily for absorbing simple fluids such as urine, are typically available from various commercial vendors, such as, for example, Dow Chemical Company or Stockhausen, Inc.

The method by which AUL is determined is set forth in greater detail below. The AUL is thought to be a function of the following factors: (1) gel stiffness while swelling, (2) ability to imbibe the fluid by osmotic and internal electrostatic repulsion forces, (3) surface wettability of the superabsorbent material and (4) particle size distribution when wet.

Suitably, the superabsorbent material is in the form of particles which, in the unswollen state, have maximum cross-sectional diameters ranging between about 50 and about 1,000 microns; desirably, between about 100 and about 800 microns; more desirably, between about 200 and about 650 microns; and most desirably, between about 300 and about 600 microns, as determined by sieve analysis according to American Society for Testing Materials Test Method D-1921. It is understood that the particles of superabsorbent material may include solid particles, porous particles, or may be agglomerated particles including many smaller particles agglomerated into particles falling within the described size ranges.

The superabsorbent-containing composites of the present invention also include at least a first layer of at least one particle of at least one coating material. In such an instance, the first layer of coating material is in intimate association with and covering the superabsorbent material. The coating material of the first layer is desirably in particle form and capable of selectively removing at least a portion of an amount of at least one specific component of a complex fluid. Typically, it is desired that the one or more specific components selectively removed by the coating material of the first layer be different than the one or more specific components selectively removed by the superabsorbent material of the superabsorbent-containing composite. It is, however, within the scope of the present invention that the one or more specific components selectively removed by the coating material be similar to the one or more specific components selectively removed by the superabsorbent material. FIGS. 1 through 12 illustrate superabsorbent-containing composites of the present invention having a single or first layer of coating material.

The superabsorbent-containing composites of the present invention may also include a second layer of at least one particle of at least one coating material. In such an instance, the second layer of coating material is at least in intimate association with and covering the first layer of coating material. The coating material of the second layer is desirably in particle form and capable of selectively removing at least a portion of an amount of at least one specific component of a complex fluid. Typically, it is desired that the one or more specific components selectively removed by the coating material of the second layer be different than the one or more specific components selectively removed by either the first layer of coating material or the superabsorbent material of the superabsorbent-containing composite. It is, however, within the scope of the present invention that the one or more specific components selectively removed by the coating material of the second layer be similar to the one or more specific components selectively removed by either the first layer of coating material or the superabsorbent material of the superabsorbent-containing composite.

Use of "cover," "covers," "covering" or "covered" with regard to coating material is intended to indicate that the coating material extends over the surface of the material being covered to the extent necessary to realize many of the advantages of the present invention. Without desiring to be bound by theory, this includes situations where the coating material extends over at least about 20 percent of the surface of the material being covered; alternatively, over at least about 30 percent of the surface of the material being covered; alternatively, over at least about 40 percent of the surface of the material being covered; alternatively, over at least about 50 percent of the surface of the material being covered; alternatively, over at least about 60 percent of the surface of the material being covered; alternatively, over at least about 70 percent of the surface of the material being covered; alternatively, over at least about 80 percent of the surface of the material being covered; and finally, alternatively, over at least about 90 percent of the surface of the material being covered. The term "surface" and its plural generally refer herein to the outer or the topmost boundary of an object.

A wide variety of natural and synthetic materials, capable of selectively removing at least a portion of an amount of at least one specific component of a complex fluid, can be employed as the coating material of the present invention. Suitable coating materials therefore include adsorbent and/or absorbent material. It is, of course, desired to use coating materials that are inexpensive, readily available and safe—important attributes for a material used in the disposable absorbent articles described herein. Illustrative examples of coating material suitable for use in the present invention include particles of hydrophilic material. Examples of hydrophilic material suitable for use as coating material include, but are not limited to, cellulosic materials, both natural and synthetic, such as wood pulp and products made from it such as powdered cellulose, and non-woody cellulose materials such as cotton, linen, jute, abaca, ixtl and the like, and products made from them such as cotton linters and floc; regenerated cellulose such as rayon, cupram, lyocell and the like; and cellulose derivatives such as hydroxypropyl cellulose, hydroxyethyl cellulose, ethyl cellulose, cellulose acetate and the like. A particularly desired coating material is microcrystalline cellulose powder. Also suitable for use as coating material are silicates, both natural and synthetic, such as precipitated silica, fumed silica, silicon dioxide, zeolites, clays, vermiculite, perlite and the like. Also found suitable for use as coating material are insoluble proteins such as texturized vegetable proteins (e.g., soy protein) and zein.

It should be noted that cellulosic coating materials suitable for use in the present invention desirably do not include chemically stiffened, cellulosic fibers. As used herein, the term "chemically stiffened, cellulosic fibers" means cellulosic fibers which have been stiffened by chemical means to increase stiffness of the fibers under both dry and aqueous conditions. Such means include the addition of chemical stiffening agents which, for example, coat and/or impregnate the fibers. Such means also include the stiffening of the fibers by altering the chemical structure of the fibers themselves, e.g., by cross-linking polymer chains.

It should be further noted that the present invention is not limited to the use of only one coating material, but can also include mixtures of two or more coating materials. Although hydrophilic materials have been indicated as being suitable for use as coating materials in the present invention, one skilled in the art would readily appreciate the possibility of treating the surfaces of hydrophobic materials by an appropriate known method to render the hydrophobic materials more or less hydrophilic. As previously indicated, the coating material is in particulate form; consequently, it is understood that the particles of coating material may include solid particles, porous particles, or may be an agglomeration of more than one particle of coating material.

It should be further noted that

In various embodiments of the present invention, the intimate association of a coating material with a superabsorbent material is achieved with the use of an association agent. The association agent usually includes substances that can be applied in liquid or semi-liquid form to either the superabsorbent material or the coating material. The term "applied" as used herein is intended to include situations where: at least a portion of the surface of at least one particle of superabsorbent material has an effective amount of association agent on it to facilitate adherence, via mechanical and/or chemical bonding, of at least that portion of the surface of the superabsorbent material to a portion of the surface of at least one particle of coating material; at least a portion of the surface of at least one particle of coating material has an effective amount of association agent on it to facilitate adherence, via mechanical and/or chemical bonding, of at least that portion of the surface of the coating material to a portion of the surface of at least one particle of superabsorbent material; and/or at least a portion of the surface of at least one particle of coating material has an effective amount of association agent on it to facilitate adherence, via mechanical and/or chemical bonding, of at least that portion of the surface of the coating material to a portion of the surface of at least one other particle of coating material. Desirably, the association agent is applied to the selected material in an amount of from about 90:10 to about 10:90, by weight.

The selection of a particular association agent can be made by one skilled in the art and will typically depend upon the chemical composition of the materials to be maintained in intimate association with one another. Desirably, the association agent is suitable for use in applications involving human contact. Thus, the association agent should be non-toxic and non-irritating to humans. An association agent suitable for use in the present invention is typically prepared by the formation of a liquid or semi-liquid capable of being generally uniformly atomized. In particular, a solution, dispersion or emulsion including at least one of the association agents identified herein may be prepared. Although the association agent is described herein as being applied as finely atomized droplets, it may be applied to the selected material by any other method such as by spraying in liquid or semi-liquid form, spraying and blowing in the form of steam, and the like.

Several types of association agent are capable of being employed in the present invention. Illustrative association agents suitable for use in various embodiments of the present invention include, for example: water; volatile organic solvents such as alcohols; aqueous solutions of film-forming materials such as dried milk, lactose, soluble soy protein, and casein; synthetic adhesives such as polyvinyl alcohol; and mixtures thereof. The presence of water in the association agent is particularly effective in predisposing the superabsorbent material to wetting.

As used herein, the phrase "absorbent article" refers to devices which absorb and contain body fluids, and more specifically, refers to devices which are placed against or near the skin to absorb and contain the various fluids discharged from the body. The term "disposable" is used herein to describe absorbent articles that are not intended to be laundered or otherwise restored or reused as an absorbent article after a single use. Examples of such disposable absorbent articles include, but are not limited to: health care related products including ostomy products, surgical drapes, gowns, and sterilization wraps; personal care absorbent products such as feminine hygiene products, diapers, training pants, incontinence products and the like; as well as facial tissues.

Disposable absorbent articles such as, for example, many of the personal care absorbent products, typically include a fluid pervious topsheet, a liquid impervious backsheet joined to the topsheet and an absorbent core positioned between the topsheet and the backsheet. Disposable absorbent articles and components thereof, including the topsheet, backsheet, absorbent core and any individual layers of these components, generally have a body-facing surface and a garment-facing surface. As used herein, "body-facing surface" refers to that surface of the article or component which is intended to be worn toward or placed adjacent to the body of the wearer, while the "garment-facing surface" is on the opposite side and is intended to be worn toward or placed adjacent to the wearer's undergarments when the disposable absorbent article is worn.

The superabsorbent-containing composites of the present invention are suitable for use in a variety of disposable absorbent articles. In general, the superabsorbent-containing composites may be used in a manner similar to that in which other absorbent composites have been used: for example, in laminates, in relatively high density cores (i.e., compacted cores, calendered cores, densified cores, etc.), or in relatively low density cores (i.e., not compacted, for example, air-laid cores). However, the superabsorbent-containing composites of the present invention provide certain advantages over conventional absorbent composites. In particular, the superabsorbent-containing composites of the present invention demonstrate an improved efficacy in the handling of complex fluids. More particularly, the superabsorbent-containing composites of the present invention demonstrate an improved efficacy in the handling of menses. As a result of this improved efficacy, the incorporation of the superabsorbent-containing composites of the present invention into feminine hygiene products such as, for example, sanitary napkins and panti-liners, results in many users of such products experiencing a sense of increased dryness. In addition, feminine hygiene products incorporating the superabsorbent-containing composites of the present invention may be made thinner while being able to absorb substantially similar amounts of menses as is absorbed by much thicker feminine hygiene products that do not contain the superabsorbent-containing composites of the present invention.

The superabsorbent-containing composites of the present invention may be prepared in a manner similar to fluidized bed coating processes. In one embodiment of such a process, at least one particle of a coating material is suspended in a fluidized bed coating apparatus that creates a strong upward current or stream of fluidizing gas, usually air, typically at an inlet temperature approximating that of room temperature. The strong upward current or stream of fluidizing gas moves the coating material upward until the coating material passes out of the upward stream and passes downward in a fluidized condition countercurrent to the upward stream of fluidizing gas. The coating material may re-enter the upward-moving stream of fluidizing gas. While in the upward-moving stream, the coating material passes through a zone where an association agent is applied to the coating material. After the association agent is applied to the coating material, at least one particle of superabsorbent material is introduced into the apparatus. A strong upward current or stream of fluidizing gas, usually air, optionally at an elevated inlet temperature (i.e., a temperature typically above room temperature), moves the coating material and the superabsorbent material upward until the coating material and the superabsorbent material pass out of the upward stream and pass downward in a fluidized condition countercurrent to the upward stream of fluidizing gas. The coating material and the superabsorbent material may re-enter the upward-moving stream of fluidizing gas until a superabsorbent-containing composite is formed. It is typically after the association agent is applied that the coating material comes into intimate association with the superabsorbent material to form a superabsorbent-containing composite. The superabsorbent-containing composite so formed includes at least one particle of superabsorbent material covered with at least a first layer of at least one particle of coating material. The coating material of the first layer is in intimate association with and covering the surface of the superabsorbent material.

The superabsorbent-containing composites of the present invention may also be prepared by another embodiment of the process described herein. In this embodiment, at least one particle of a superabsorbent material is suspended in a fluidized bed coating apparatus that creates a strong upward current or stream of fluidizing gas, usually air, typically at an inlet temperature approximating that of room temperature. The strong upward current or stream of fluidizing gas moves the superabsorbent material upward until the superabsorbent material passes out of the upward stream and passes downward in a fluidized condition countercurrent to the upward stream of fluidizing gas. The superabsorbent material may re-enter the upward-moving stream of fluidizing gas. While in the upward-moving stream, the superabsorbent material passes through a zone where an association agent is applied to the superabsorbent material. After the association agent is applied to the superabsorbent material, at least one particle of coating material is introduced into the apparatus. A strong upward current or stream of fluidizing gas, usually air, optionally at an elevated inlet temperature, moves the coating material and the superabsorbent material upward until the coating material and the superabsorbent material pass out of the upward stream and pass downward in a fluidized condition countercurrent to the upward stream of fluidizing gas. The coating material and the superabsorbent material may re-enter the upward-moving stream of fluidizing gas until a superabsorbent-containing composite is formed. It is typically after the association agent is applied that the coating material comes into intimate association with the superabsorbent material to form a superabsorbent-containing composite. The superabsorbent-containing composite so formed includes at least one particle of superabsorbent material covered with at least a first layer of at least one particle of coating material. The coating material of the first layer is in intimate association with and covering the surface of the superabsorbent material.

The superabsorbent-containing composites of the present invention may also be prepared by still another embodiment of the process described herein. In this embodiment, at least one particle of coating material and at least one particle of superabsorbent material are suspended in a fluidized bed coating apparatus that creates a strong upward current or stream of fluidizing gas, usually air, typically at an inlet temperature approximating that of room temperature. The strong upward current or stream of fluidizing gas moves both the coating material and the superabsorbent material upward until the coating material and the superabsorbent material pass out of the upward stream and pass downward in a fluidized condition countercurrent to the upward stream of fluidizing gas. The coating material and the superabsorbent material may re-enter the upward-moving stream of fluidizing gas. While in the upward-moving stream, the coating material and the superabsorbent material pass through a zone where an association agent is applied to both the coating material and superabsorbent material. After the association agent is applied, the strong upward-moving stream of fluidizing gas, usually air, optionally at an elevated inlet temperature, moves the coating material and the superabsorbent material upward until the coating material and the superabsorbent material pass out of the upward stream and pass downward in a fluidized condition countercurrent to the upward stream of fluidizing gas. The coating material and the superabsorbent material may re-enter the upward-moving stream of fluidizing gas until a superabsorbent-containing composite is formed. It is typically after the association agent is applied that the coating material comes into intimate association with the superabsorbent material to form a superabsorbent-containing composite. The superabsorbent-containing composite so formed includes at least one particle of superabsorbent material covered with at least a first layer of at least one particle of coating material. The coating material of the first layer is in intimate association with and covering the surface of the superabsorbent material.

Figure 13:
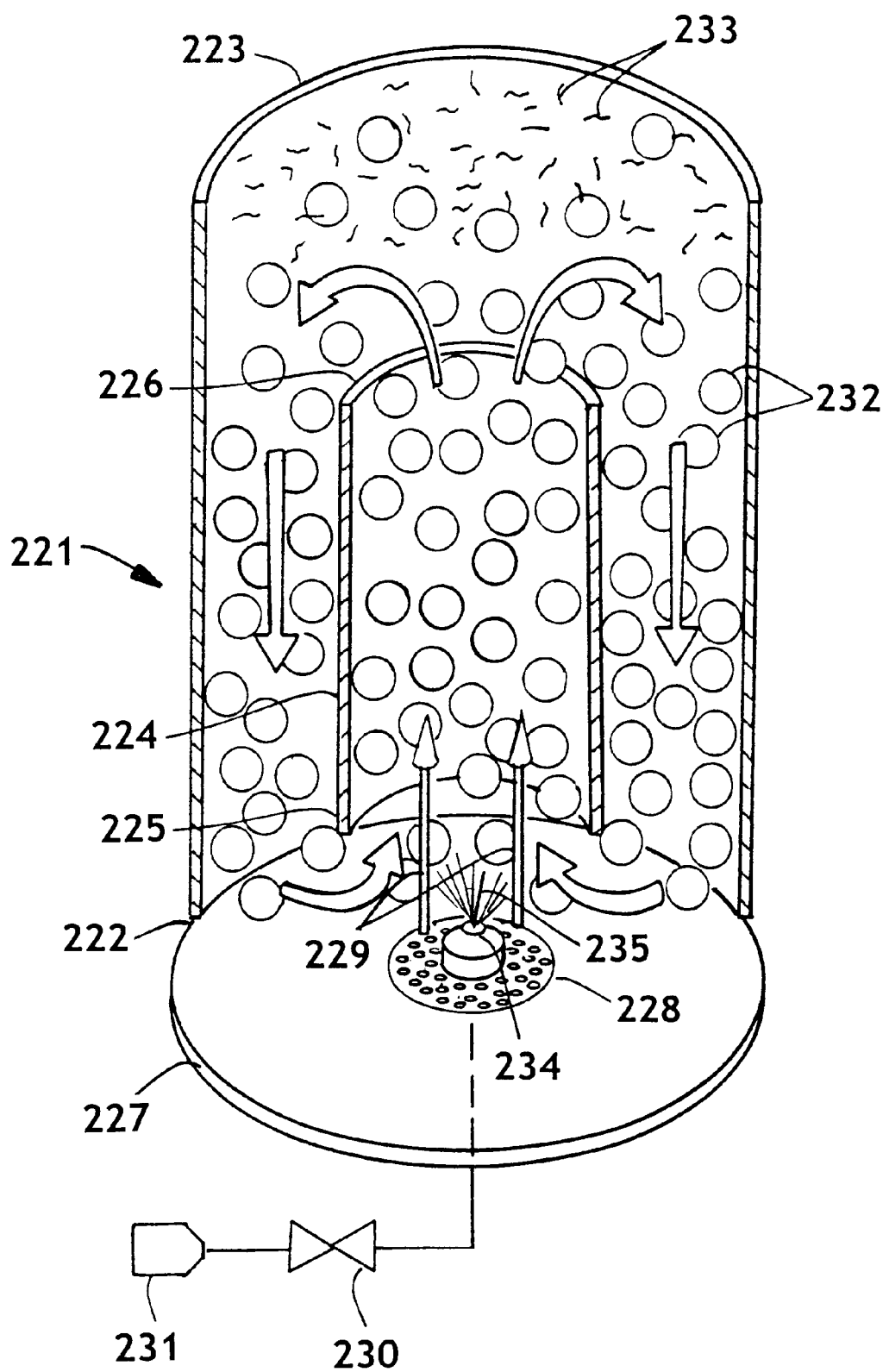
FIG. 13 illustrates a representative fluidized bed coating apparatus.

Typically, a fluidized bed coating apparatus similar to that illustrated in FIG. 13 can be utilized to form the superabsorbent-containing composites of the present invention. Referring to FIG. 13, a generally vertically-mounted, generally cylindrical chamber (221) is open at chamber proximal end (222) and closed at chamber distal end (223). The chamber (221) is optionally provided with an inner chamber (224) that has a diameter less than that of the chamber. The inner chamber (224) is open at both inner chamber proximal end (225) and inner chamber distal end (226). The chamber proximal end (222) is fitted with a plate (227) that has a porous area (228) that generally matches the diameter of the inner chamber (224). The inner chamber (224) is positioned a distance above the plate (227) and is generally aligned along the vertical axis of the chamber (221). Through the porous area (228) is provided an upward current or stream (229) of fluidizing gas, usually air, typically at an inlet temperature approximating that of room temperature, such as from a valve (230) from a source of compressed gas (231). The upward-moving stream (229) of fluidizing gas generally flows through the inner chamber (224) by entering through the inner chamber proximal end (225) and exiting through the inner chamber distal end (226). As described in one of the previously mentioned process embodiments, at least one particle of coating material (233) is introduced into the chamber (221). The upward-moving stream (229) of fluidizing gas is adjusted so as to provide a fluid-like flow to the coating material (233). The upward-moving stream (229) of gas moves the coating material (233) upward until the coating material passes out of the upward stream and passes downward in a fluidized condition countercurrent to the upward-moving stream of fluidizing gas. The coating material (233) may re-enter the upward-moving stream (229) of fluidizing gas. While in the upward-moving stream, the coating material passes through a zone where an association agent (235) is applied to the coating material (233). This zone is generally located in the vicinity of a sprayer means (234) positioned near the center of the plate (227). After the association agent is applied to the coating material (233), at least one particle of superabsorbent material (232) is introduced into the chamber (221). If necessary, the upward-moving stream (229) of gas is adjusted so as to provide a fluid-like flow to the superabsorbent material (232) and the coating material (233). After introduction of the superabsorbent material (232), the inlet temperature of the upward-moving stream (229) of fluidizing gas is optionally elevated to a temperature in excess of room temperature. The cyclic flow of the superabsorbent material (232) and the coating material (233) is generally allowed to continue in the chamber (221) until the coating material comes into intimate association with the superabsorbent material to form a superabsorbent-containing composite. The superabsorbent-containing composite is then recovered or removed from the chamber (221). The superabsorbent-containing composite so formed includes at least one particle of superabsorbent material covered with at least a first layer of at least one particle of coating material. The coating material of the first layer is in intimate association with and covering the surface of the superabsorbent material.

A fluidized bed coating process is relatively mild in its effect on the superabsorbent material being brought into intimate association with the coating material and is therefore less damaging to the microstructure of the superabsorbent material as compared to other processes. Although discussed in terms of being formed in a fluidized bed coating process, the superabsorbent-containing composites of the present invention may also be formed using a variety of other processes incorporating, for example, a V-shell blender or other apparatus that is relatively mild in its effect on the superabsorbent material.

Optionally, after formation, the superabsorbent-containing composite of the present invention may remain in the apparatus and subject to the strong upward current or stream of fluidizing gas at an elevated temperature until the moisture content of the superabsorbent-containing composite is less than that which would support the growth of microorganisms. While not desiring to be bound by theory, it is believed that to minimize the likelihood of the growth of microorganisms, the moisture content of the superabsorbent-containing composites should be about 15 percent or less by weight; desirably, about 10 percent or less by weight; more desirably, about 5 percent or less by weight; and most desirably, about 3 percent or less by weight. Although embodiments of the process have been described herein as optionally drying a superabsorbent-containing composite in the apparatus, the optional drying of a superabsorbent-containing composite could be accomplished either in the apparatus or out of the apparatus according to any of a number of other drying processes known to those skilled in the art.

Depending on the intended use of a superabsorbent-containing composite, it may be desired to add a second layer of at least one particle of coating material to a superabsorbent-containing composite. The second layer of coating material, as well as any subsequent additional layer of coating material, is added in generally the same manner as is a first layer of coating material according to the at least one of the process embodiments described herein.

Although previously described herein as having a one- or two-layered configuration, it is also within the present invention to form superabsorbent-containing composites having more than two layers. Consequently, it is within the scope of the present invention to form superabsorbent-containing composites having a single layer of coating material or superabsorbent-containing composites having two or more layers of coating material in a variety of multi-layered configurations with each layer including one or more coating materials.

Various embodiments of the present process may operate at inlet temperatures ranging from about room temperature to about 72° C. The inlet temperature may, however, range considerably higher than about 72° C. so long as the bed temperature in the apparatus does not exceed a temperature that would cause decomposition of the superabsorbent-containing composite or any material included in the superabsorbent-containing composite. The selection of a particular inlet temperature would depend on the superabsorbent material, the coating material and the association agent, and may be readily selected by one skilled in the art.

It is desired that a superabsorbent-containing composite of the present invention has a weight ratio, based on the total weight of the superabsorbent material and the coating material in the superabsorbent-containing composite, of superabsorbent material to coating material of from about 45:55 to about 95:5; alternatively, from about 60:40 to about 80:20; and finally, alternatively, from about 65:35 to about 70:30. In addition, the superabsorbent-containing composite of the present invention suitably should be able to retain a complex fluid. The ability of a superabsorbent-containing composite of the present invention to retain a complex fluid is quantified herein as the complex fluid retention capacity (CFRC). The complex fluid retention capacity is a quantification of the amount of complex fluid that a superabsorbent-containing composite retains after a force has been applied. The amount of complex fluid retained is calculated as a gram per gram retention. Suitably, a superabsorbent-containing composite of the present invention has a complex fluid retention capacity, as further defined hereinbelow, of between 0 and about 20; alternatively, of between about 5 and about 20; alternatively, of between about 10 and about 20; alternatively, of between about 12 and about 20; alternatively, of between about 13 and about 20; alternatively, of between about 15 and about 20; and finally, alternatively, of between about 18 and about 20 g/g.

Figure 14:
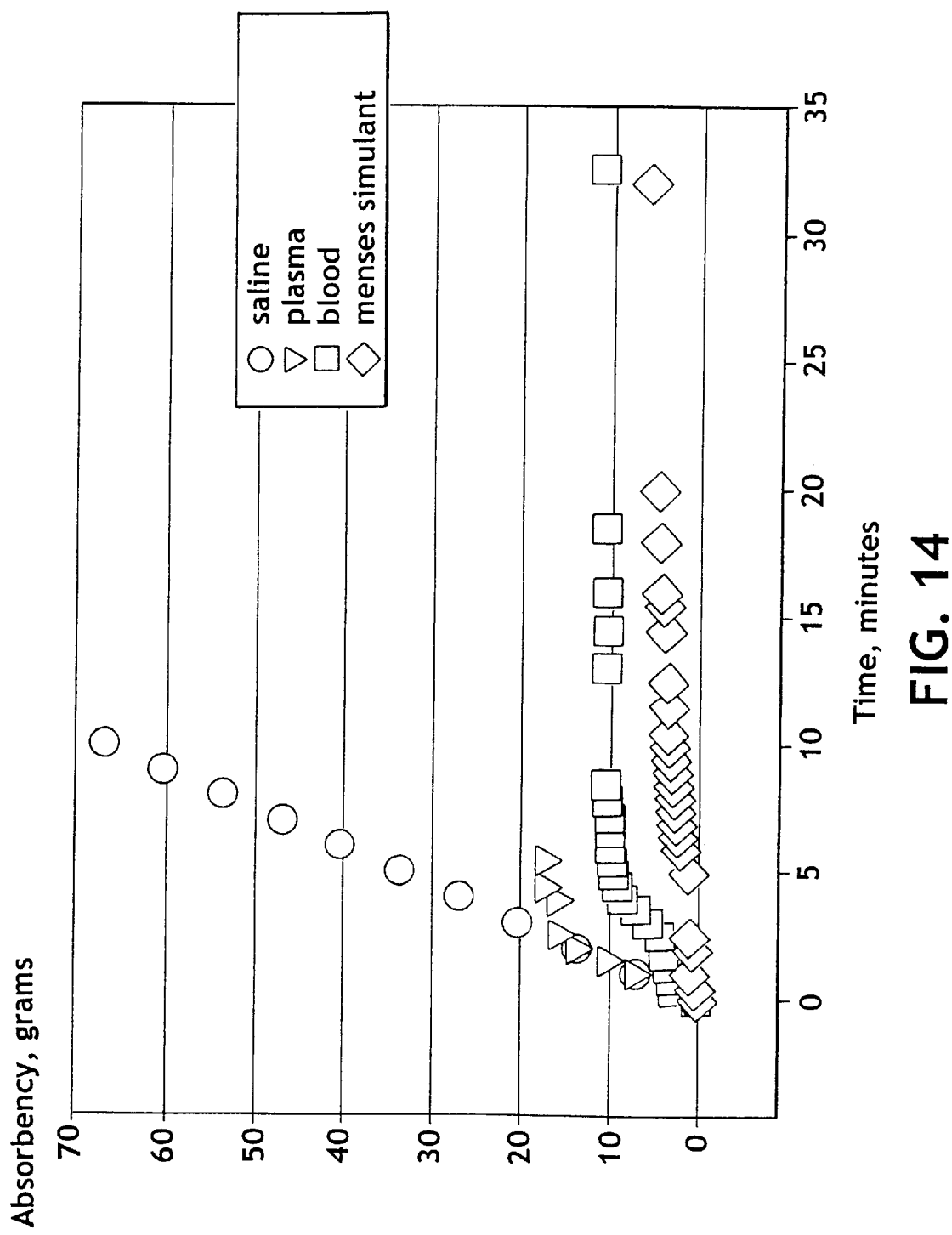
FIG. 14 illustrates a plot of one set of data obtained according to the On Demand Intake Test when performed using an uncoated superabsorbent material.
Figure 15:
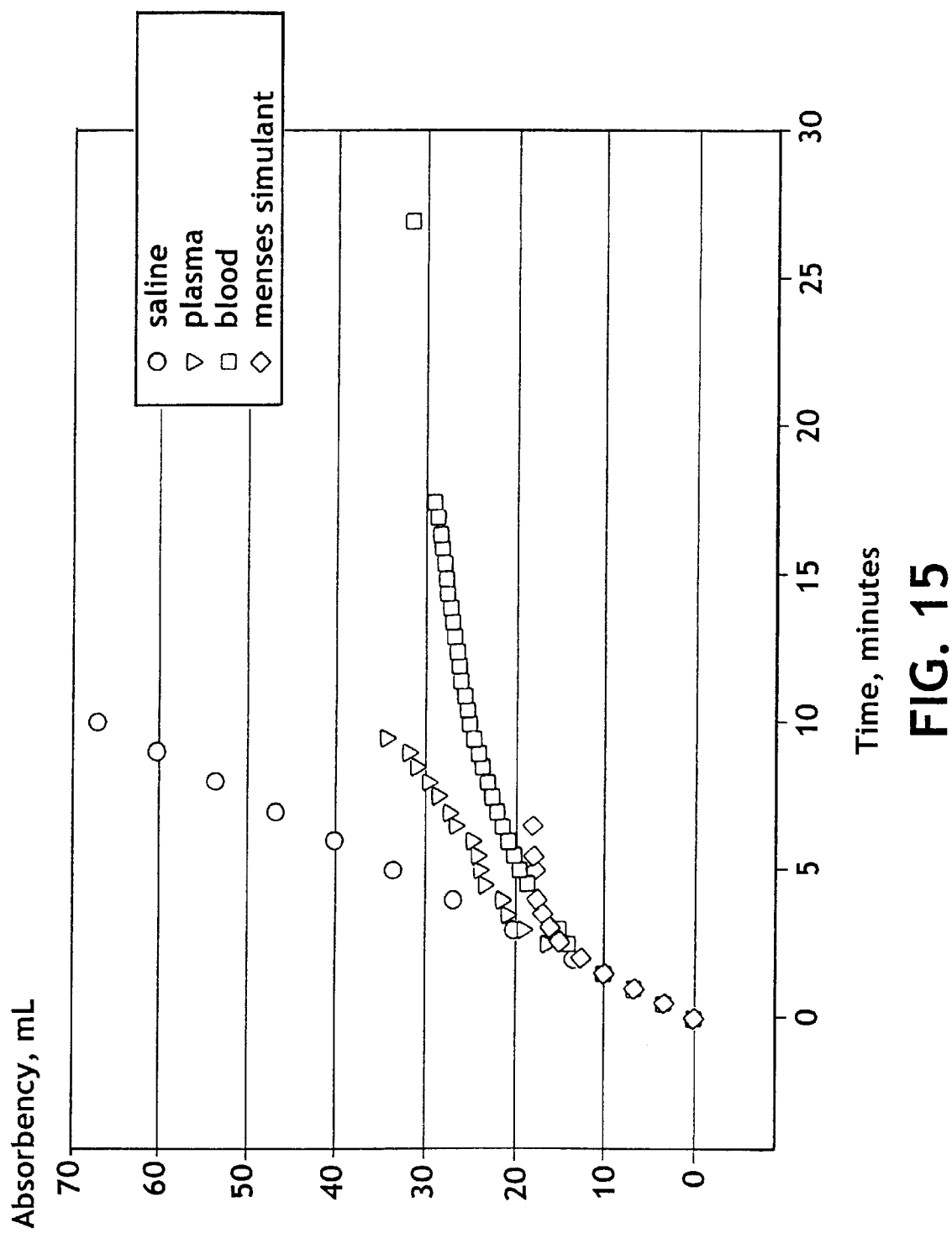
FIG. 15 illustrates a plot of one set of data obtained according to the On Demand Intake Test when performed using a superabsorbent-containing composite of the present invention.
Figure 16:
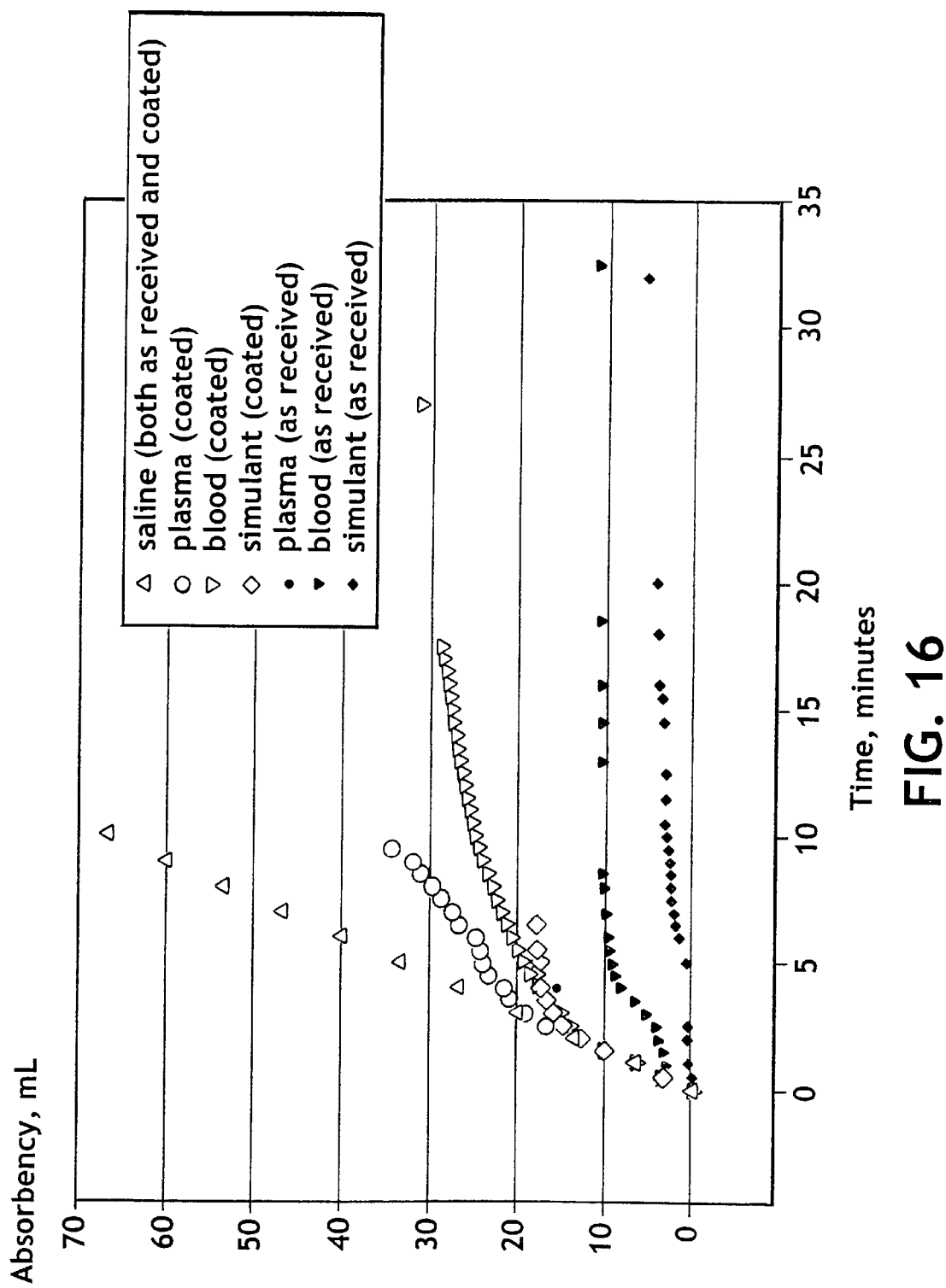
FIG. 16 illustrates a plot combining the sets of data individually illustrated in FIGS. 14 and 15.

As previously mentioned, current commercially available, mass-produced superabsorbent materials interact with complex fluids, such as menses, in a very ineffective manner. Red blood cells (constituting approximately 30 to 50 percent of typical menses samples) can adsorb onto the surface of a particle of superabsorbent material and coat the surface of the particle of superabsorbent material, both hindering the flow of fluid to the surface and providing a physical restraint, thus preventing swelling of the particle of superabsorbent material. Even in the absence of red blood cells, blood proteins have been observed to cause a similar, though somewhat less striking, reduction in capacity due to essentially the same cause—deposition of proteins on the surface of a particle of superabsorbent material. Menses, for example, contains, inter alia, mucus or mucin materials. These mucin materials can be de-watered into an essentially liquid-impermeable barrier on the surface of a particle of superabsorbent material resulting in a striking reduction in retention capacity. FIG. 14 illustrates the absorbency of an uncoated superabsorbent material (Favor SXM 880) with respect to a simple fluid such as saline and complex fluids such as menses (simulant), blood and plasma. FIG. 15 illustrates the absorbency of a superabsorbent-containing composite (Avicel-coated Favor SXM 880) of the present invention with respect to saline, menses (simulant), blood and plasma. FIG. 16 is a combination of the data illustrated individually in FIGS. 14 and 15. FIG. 16 illustrates one of the advantages that can be obtained from the superabsorbent-containing composites of the present invention; namely, an improved efficacy in the handling of complex fluids when compared to relatively inexpensive and readily obtainable superabsorbent materials that have typically been developed primarily to absorb simple fluids.

The relatively larger components—generally considered as those components having a diameter greater than about five microns—of a complex fluid can adsorb onto and coat the surface of a particle of superabsorbent material, thus mitigating the efficacy of a superabsorbent material in the handling of a complex fluid. In one embodiment of the superabsorbent-containing composite of the present invention, an improved efficacy in the handling of a complex fluid is achieved when the coating material substantially inhibits those components of a complex fluid having a diameter of greater than about five microns from being adsorbed onto the surface of the superabsorbent material of the superabsorbent-containing composite.

Since adsorption of cells and molecules generally takes place at the surface of a coating material, a process which increases either the surface area of the coating material or the surface activity of the coating material toward the adsorption of specific cells and molecules would typically increase the retention capacity of the superabsorbent material by delivering fewer of the interfering substances to the surface of the superabsorbent material. One means of increasing the surface area of a suitable coating material would be to attrite the surface of the coating material. Another means of increasing the surface area of a suitable coating material would be to etch the surface of the coating material. Regardless of the surface area, a surface can be made more active, and thus more attractive to specific components of a complex fluid by chemical modification. A particularly simple and inexpensive method of modifying the surface activity of a material is to add a cationic debonding agent. Typical cationic debonding agents include quaternary amino compounds such as, for example, a quaternary ammonium salt of a fatty acid. As is well known to those who process wood pulp fibers, an aqueous solution of a debonding agent will spontaneously coat a cellulose surface. In the case of a cationic debonding agent, the cellulose surface will then become positively charged and will more effectively adsorb negatively charged red blood cells and blood proteins. A cellulose surface could also be directly derivatized, for example, by reaction to form diethylamino cellulose, a well known and easily prepared positively charged derivative. Again, the positive charge on the derivatized cellulose surface will more effectively remove cells and proteins from blood and menses.

Test Methods

Absorbency Under Load (AUL)

Figure 17:
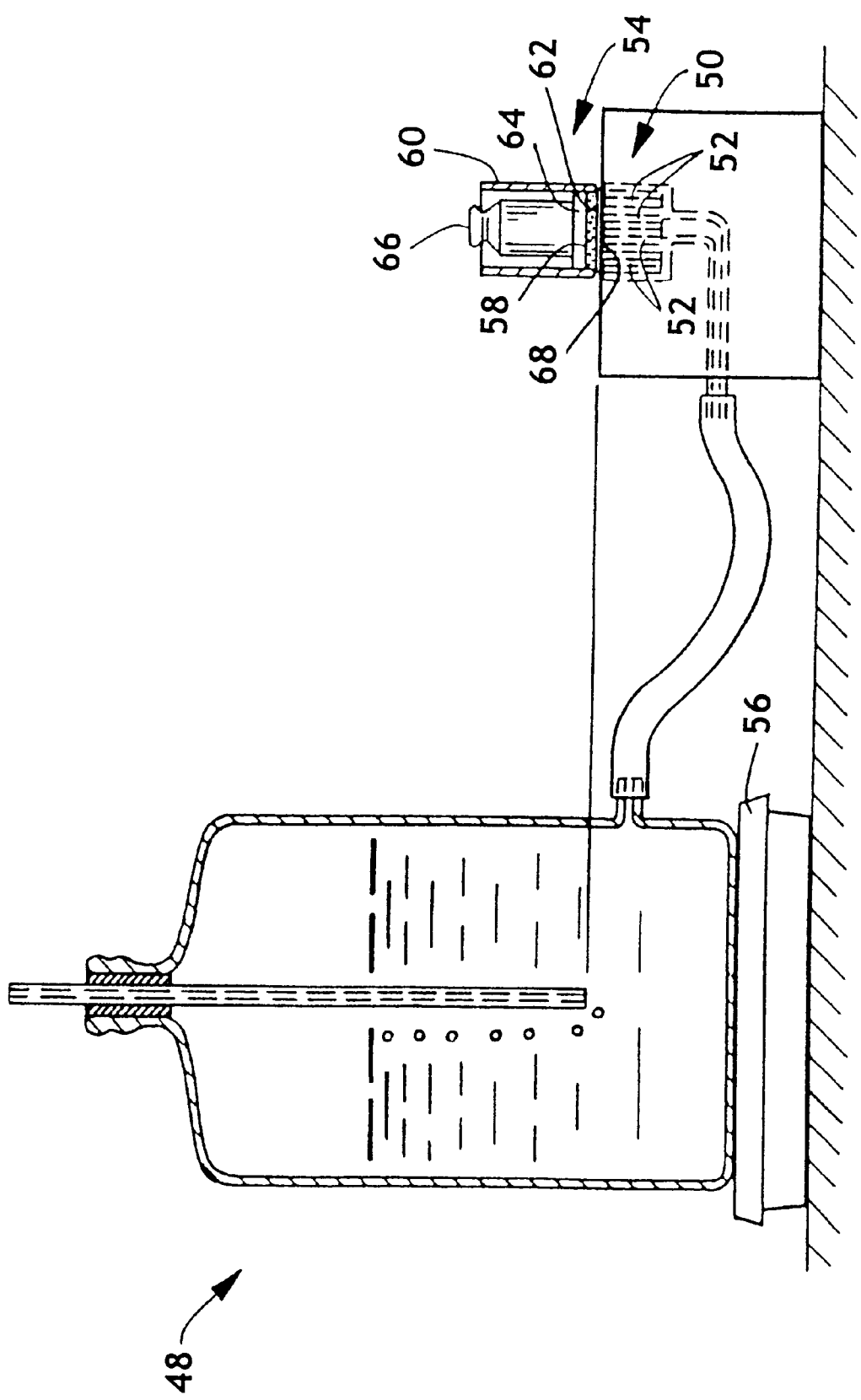
FIG. 17 is an illustration of equipment suitable for determining the Absorbency Under Load (AUL) of superabsorbent material.

The ability of a superabsorbent material to absorb a liquid while under a load is determined as follows. With reference to FIG. 17, a Demand Absorbency Tester (DAT) (48) is used, which is similar to the GATS (Gravimetric Absorbency Test System), available from M/K Systems, Danners, Mass. USA, as well as the system described by Lichstein at pages 129–142 of the INDA Technological Symposium Proceedings, March 1974. A porous plate (50) is used, having ports (52) confined within a 2.5 centimeter diameter area and covered by the Absorbency Under Load (AUL) apparatus (54). An electrobalance (56) is used to measure the flow of fluid into the superabsorbent particles (58). For this test, the fluid employed is an aqueous solution containing 0.9 weight percent sodium chloride used at room temperature.

The AUL apparatus (54) used to contain the superabsorbent particles includes a cylinder (60) made from 1 inch (2.54 centimeters) inside diameter thermoplastic tubing which is machined-out slightly to be sure of concentricity. A 100 mesh stainless steel wire cloth (62) is adhered on the bottom of cylinder (60) by means of an adhesive. Alternatively, the stainless steel wire cloth (62) can be fused to the bottom of cylinder (60) by heating the wire cloth in a flame until red hot, after which the cylinder is held onto the cloth until cooled. A soldering iron can be used to touch up the seal if unsuccessful or if it breaks. Care must be taken to maintain a flat, smooth bottom, and not distort the inside of the cylinder. A 4.4 gram piston (64) is made from 1 inch diameter solid material (e.g., Plexiglas™ and is machined to closely fit without binding in the cylinder (60). The piston (64) is used to provide the restraining load of 0.01 pound per square inch. A weight (66) is used to provide the greater degrees of restraining load. As discussed above, the greater restraining loads are 0.29 pound per square inch, 0.57 pound per square inch, and 0.90 pound per square inch. Accordingly, a 100, 200, and 317 gram weight is used to provide the respective restraining loads (in addition to the 4.4 gram piston (64)). A sample of superabsorbent particles weighing 0.160 (±0.005) gram is utilized for testing AUL. The sample is taken from granules which are pre-screened through US standard 30 mesh and retained on US standard 50 mesh (300–600 microns). The particles, when tested, have a moisture content of less than about 5 weight percent.

This test is initiated by placing a 3 centimeter diameter GF/A glass filter paper (68) onto the plate (50). The paper is sized to be larger than the internal diameter and smaller than the outside diameter of the cylinder (60) to ensure good contact while eliminating evaporation over the ports (52) of the DAT (48) and then allowing saturation to occur. The particles (58) are weighed on weighing paper and placed on the wire cloth (62) at the bottom of the AUL apparatus (54). The apparatus (54) is shaken to level the particles (58) on the wire cloth (62). Care is taken to be sure no particles are clinging to the wall of the cylinder (60). After carefully placing, without pressing, the piston (64) and, optionally, the weight (66) on the particles (58) in the cylinder (60), the AUL apparatus (54) is placed on the glass filter paper (68). The amount of fluid picked up is monitored as a function of time either directly by hand, with a strip-chart recorder, or directly into a data acquisition or personal computer system.

The amount (in grams) of fluid picked up after 60 minutes, divided by the weight of the sample (0.160 gram), is the AUL value in grams of fluid picked up per gram of sample (g/g). The rate of fluid picked up can also be measured. Two checks can be made to ensure the accuracy of the instantaneous final readout. First, the height the piston (64) rises multiplied by the cross-sectional area of the cylinder (60) should nearly equal the amount of fluid picked up. Second, the AUL apparatus (54) can be weighed before and after the test and the difference in weight should nearly equal the fluid picked up. A minimum of three tests are performed on a given sample and averaged to assign an AUL value.

Absorbency Rate and Rewet Test Method

As used herein, the Absorbency Rate and Rewet Test Method measures at least the following two characteristics of absorbent materials:

1. Absorbency rate—the amount of time, in seconds, it takes for a known amount of absorbent material to absorb multiple insults of known quantities of a fluid; and
2. Rewet—the amount of fluid, in grams, that is released from the absorbent material when blotter paper is placed on top of the absorbent material and a known pressure is applied for a predetermined period of time.

Testing according to this method consisted of using a stopwatch to determine the amount of time, in seconds, required for 20 mL of absorbent material to absorb multiple insults (3 or 6 mL) of fluid. A Harvard Syringe Pump is programmed to dispense 6 mL of fluid onto 20 mL of absorbent material, at which time a stopwatch is simultaneously started. The stopwatch is stopped when the 6 mL of fluid is absorbed into the absorbent material. A second insult of 6 mL is then dispensed and timed. The second insult is followed by a third insult, this time consisting of 3 mL, which is also timed. This results in a total of 15 mL and three timed insults. Wait approximately 60 seconds from absorption of the third insult before placing a pre-weighed blotter paper onto the 20 mL of absorbent material and applying a 0.5 psi pressure for 60 seconds. After 60 seconds, the blotter paper is reweighed and the fluid, in grams, that has been absorbed by the blotter paper is considered the amount of rewet. Testing is typically conducted under TAPPI Standard Conditions.

Equipment and Materials:

Harvard Apparatus Programmable Syringe Pump, Model No. 44, commercially available from Harvard Apparatus, South Natick, Mass. 01760 USA.

The fluid in this instance, by way of example only and not by way of limitation, is an artificial menses (simulant), disclosed in U.S. Pat. No. 5,883,231, issued Mar. 16, 1999, to Achter et al., the disclosure of which is hereby incorporated herein by reference to the extent that said disclosure is consistent (i.e., not contradictory) with the present specification. The simulant disclosed and claimed in U.S. Pat. No. 5,883,231 is commercially available from Cocalico Biologicals, Inc., 449 Stevens Rd., P.O. Box 265, Reamstown, Pa. 17567 USA.

Disposable plastic weighing boats commercially available from NCL of Wisconsin, Inc., Birnamwood, Wis. 54414 USA, part number W-D 80055.

60 cc disposable syringe, commercially available from Becton Dickinson, Franklin Lakes, N.J. 07417 USA; Tygon tubing, size 16 with 0.12 inch inner diameter, part number 6409-16, commercially available from Cole-Parmer Instrument Company, Chicago, Ill. 60648 USA; and ⅛ inch outer diameter hose, barb size, part number R-3603 and also commercially available from Cole-Parmer Instrument Company.

5.5 cm blotter paper, commercially available from VWR Scientific Products, 1145 Conwell Ave., Willard, Ohio 44890 USA, catalogue number 28310-015.

Weight, made by taking a 100 mL Pyrex beaker and filling it with any suitable substance to 717.5 grams to obtain a 0.5 psi loading.

Balance, readable to 0.001 g (Note: standards should be NIST traceable and should be recertified at a frequency adequate to assure accuracy).

Stopwatch, readable to 0.1 s (Note: stopwatch should be NIST traceable).

Graduated cylinder readable to 20 mL.

Clear acrylic plate (of a size sufficient to be supported on top of a disposable plastic weighing boat) with a hole drilled approximately in the center thereof for insertion of the Tygon tubing.

Specimen Preparation:

The simulant is removed from a refrigeration unit, placed on a rotator and then gently rotated for approximately 30 minutes to thoroughly mix the contents and bring the simulant to room temperature.

The graduated cylinder is placed onto the balance and the weight tared. 20 mL of absorbent material is introduced into the graduated cylinder. The graduated cylinder is removed from the balance. The bottom of the graduated cylinder is gently tapped on the top of the lab bench or similar hardened surface approximately 10 times to induce settling. Visual inspection is made to ensure that there is 20 mL of absorbent material in the graduated cylinder. The 20 mL of absorbent material is poured into a weighing boat and the absorbent material is gently leveled.

The Harvard Syringe Pump is set to the Program Mode. The Infuse Rate is set to 12 mL/min. with the Target Volume set to 6 mL. Diameter is set to the correct syringe size. The Harvard Syringe Pump is filled with approximately 60 mL of simulant.

The steps of the testing method are as follows:

1. One end of the Tygon tubing is inserted through the hole in the acrylic plate.
2. The acrylic plate is placed over a weighing boat containing 20 mL of absorbent material. The Tygon tubing should be placed approximately over the center of the absorbent material.
3. Simultaneously start the stopwatch and begin dispensing the first 6 mL insult of simulant.
4. Stop the stopwatch when the simulant is absorbed by the absorbent material. The reading on the stopwatch is recorded as "Insult 1" in seconds. In the event that the simulant is not absorbed by the absorbent material being tested (i.e., the simulant sits on the top of the absorbent material) within five minutes, stop the test and record 300+ seconds.
5. Simultaneously start the stopwatch and begin dispensing the second 6 mL insult of simulant.
6. Stop the stopwatch when the simulant is absorbed by the absorbent material. The reading on the stopwatch is recorded as "Insult 2" in seconds. In the event that the simulant is not absorbed by the absorbent material being tested (i.e., the simulant sits on the top of the absorbent material) within five minutes, stop the test and record 300+ seconds.
7. Simultaneously start the stopwatch and begin dispensing the simulant. In this instance, however, the Harvard Syringe Pump is halted after 3 mL of simulant has been dispensed.
8. Stop the stopwatch when the 3 mL of simulant is absorbed by the absorbent material. The reading on the stop watch is recorded as "Insult 3" in seconds. Once again, should the simulant not be absorbed by the absorbent material being tested (i.e., the simulant sits on the top of the absorbent material) within five minutes, stop the test and record 300+ seconds.
9. Wait 60 seconds after absorption of the third insult.
10. Weigh two pieces of blotter paper and record this weight as "BP Dry."
11. At the end of the 60 seconds noted in step 9, gently place the blotter paper on the absorbent material and then gently place the 0.5 psi weight onto the blotter paper and start the stopwatch.
12. After 60 seconds, remove the weight and reweigh the blotter paper. This weight of the blotter paper is recorded as "BP Wet."

Steps 3 through 12 outlined above are repeated until the simulant is no longer absorbed by the absorbent material (i.e., the simulant sits on the top of the absorbent material and is not absorbed within five minutes).

The results of the rewet portion of the test method are recorded in grams and calculated as follows:

$$(\text{BP Wet}) - (\text{BP Dry}) = \text{Rewet}$$

Method for Determining Retention Capacity

As used herein, the Method for Determining Retention Capacity measures the amount of test fluid that a sample of material retains after a centrifugal force has been applied. The amount of fluid retained is calculated as a gram per gram retention. The test is typically conducted under TAPPI Standard Conditions. When the test fluid is a complex fluid, such as, for example, blood, menses, artificial menses (simulant), loose passages, nasal discharges and the like, the retention capacity of a material is sometimes referred to as a complex fluid retention capacity (CFRC).

In general, testing according to this method is performed by placing a 0.5 g sample of material into a modified cylinder, exposing the sample of material to a desired fluid for 60 minutes and then placing the cylinders into a centrifuge to remove excess fluid. The results are calculated to obtain the grams of fluid retained per gram of sample of material.

Equipment and Materials:

Artificial menses fluid (simulant), disclosed in U.S. Pat. No. 5,883,231, issued Mar. 16, 1999, to Achter et al. The simulant disclosed and claimed in U.S. Pat. No. 5,883,231 is commercially available from Cocalico Biologicals, Inc. 449 Stevens Rd., P.O. Box 265, Reamstown, Pa. 17567 USA.

Sorvall RT 6000D centrifuge, commercially available from Global Medical Instrumentation, Inc., 3874 Bridgewater Dr., St. Paul, Minn. 55123 USA.

Four 200 mL, screw top centrifuge bottles, commercially available from International Equipment Co., 300 Second Ave., Needham Heights, Mass. 02494 USA.

Balance, readable to 0.001 g (Note: standards should be NIST traceable and should be recertified at a frequency adequate to assure accuracy).

Four 50 mL Pyrex beakers.

Lab timer, 60 minute capacity, readable to one second, commercially available from VWR Scientific Products, 1145 Conwell Ave., Willard, Ohio 44890 USA.

Four modified Lexan cylinders, 9 cm high, 3.1 cm ID, 4.8 cm OD, with a 300 holes/in$^2$ screen attached to the bottom.

US standard 30 and 50 screen sieves, 8 inch diameter, 2 inch height, commercially available from VWR Scientific Products, 1145 Conwell Ave., Willard, Ohio 44890 USA, catalogue numbers 57334-456 and 57334-464, respectively.

Stainless steel screen, 4 holes per inch or enough open space to allow simulant to drain.

Specimen Preparation:

Prepare the sample of material by using the US standard 30 and 50 screen sieves to fractionate a sample to the 300 to 600 micron size. Store the fractionated sample of material in a sealed substantially airtight container for use when the sample or samples of material will be prepared. The modified cylinder is placed on the balance and the weight tared. Place 0.5 g±0.005 g of the fractionated sample into one of the modified cylinders. Record this weight as Sample Weight. The modified cylinder containing the sample of material is weighed and this weight is recorded as Dry Cylinder Weight. Additional samples of material are placed in the three remaining modified cylinders according to the foregoing steps.

The simulant is removed from a refrigeration unit, placed on a rotator and then gently rotated for approximately 30 minutes to thoroughly mix the contents and bring the simulant to room temperature.

The steps of the testing method are as follows:

1. Approximately 10 mL of simulant are placed into a 50 mL Pyrex beaker.
2. A modified cylinder containing the sample of material is placed into the 50 mL Pyrex beaker.
3. Approximately 15 mL of simulant are poured into the modified cylinder. This ensures that the sample of material has access to the simulant from both above and below.
4. Repeat steps 1 through 3 as necessary for any desired additional sample of material.
5. After step 4 has been completed, the timer is set for 60 minutes and started.
6. After 60 minutes have elapsed, the modified cylinders are removed from the Pyrex beakers and placed on the stainless steel screen for 60 seconds.
7. After 60 seconds, the modified cylinders are removed from the stainless steel screen and placed in the 200 mL centrifuge bottles.
8. The centrifuge bottles are placed in the centrifuge for 3 minutes at 1,200 rpm.
9. After 3 minutes, the modified cylinders are removed from the centrifuge bottles and the modified cylinders containing the samples of material are weighed. This weight is recorded as Wet Cylinder Weight.

The Retention Capacity of each sample of absorbent is then calculated according to the following formula:

$$\frac{[(\text{Wet Cylinder Weight} - \text{Dry Cylinder Weight}) - \text{Product Weight}]}{(\text{Product Weight})}$$

Where reported in any of the following examples, the Retention Capacities are an average of two samples (i.e., n=2).

On Demand Intake Test Method

The On Demand Intake Test ("ODI Test") allows measurement of several characteristics of absorbent materials and systems containing such absorbent materials. These characteristics include absorption rate (i.e., volume of fluid that an absorbent material is able to absorb as a function of time) and capacity (i.e., the maximum volume that an absorbent material is able to absorb before becoming saturated). Indirectly, the ODI Test provides an indication of the ability of the structure of the superabsorbent-containing composites of the present invention, to wick or to block the fluid distributed within the sample being tested. The test is typically conducted under TAPPI Standard Conditions.

Specifically, the ODI Test measures the ability of an absorbent material to absorb fluid as a function of time. A pump delivers fluid to the absorbent material at a fixed flow rate (400 mL/h for the Examples herein). Once the absorbent material can no longer absorb any additional fluid, the fluid accumulates on top of the absorbent material and eventually comes into communication with a second electrode. By coming into communication with the second electrode, a circuit is closed allowing a signal to be sent that stops the pump. When the fluid is absorbed by the absorbent material, the fluid is no longer in communication with the second electrode and the circuit is opened. The opening of the circuit sends a signal that restarts the pump. During fluid delivery, the pump will stop and restart several times as a function of the rate of absorption of the absorbent material. If the pump does not stop, it means that the absorbent material is able to intake fluid at the delivery rate. Occasionally, the absorbent material is able to intake fluid at the delivery rate for the first two to five milliliters, then the absorption rate diminishes. The volume of fluid delivered by the pump as a function of time is recorded by a personal computer for the purpose of plotting a curve illustrating the rate of absorption of the absorbent material.

Equipment and Materials:

Harvard Apparatus Programmable Syringe Pump, Model No. 44, commercially available from Harvard Apparatus, South Natick, Mass. 01760 USA.

Minimum system requirements for a personal computer ("PC"): INTEL® compatible 486/33 computer with 8 MB RAM and one unused serial communication port.

WINDOWS® 95 software from Microsoft Corp., Redmond Wash. USA.

Harvard Apparatus Symphony Pump Manager software, Version 1.0, commercially available from Harvard Apparatus, South Natick, Mass. 01760 USA.

Serial cable, purchased from Harvard Apparatus, South Natick, Mass. 01760 USA, for connection between port number 1 (RJ11pin) of the Harvard Apparatus Programmable Syringe Pump and the PC serial port (PC DB-9 pin).

Liquid level control relay switch, Model No. LNC-NS132-120 available from AMETEK NCC—National Controls Corp., 1725 Western Dr., West Chicago, Ill. 60185 USA.

Unprocessed swine blood (blood), commercially available from Cocalico Biologicals, Inc., 449 Stevens Rd., P.O. Box 265, Reamstown, Pa. 17567 USA.

Swine plasma (plasma), commercially available from Cocalico Biologicals, Inc., 449 Stevens Rd., P.O. Box 265, Reamstown, Pa. 17567 USA.

Artificial menses fluid (simulant), disclosed in U.S. Pat. No. 5,883,231, issued Mar. 16, 1999, to Achter et al. The simulant disclosed and claimed in U.S. Pat. No. 5,883,231 is commercially available from Cocalico Biologicals, Inc. 449 Stevens Rd., P.O. Box 265, Reamstown, Pa. 17567 USA.

Blood bank saline (saline) having a pH of 7.2, catalogue number 8504, commercially available from New England Reagent Laboratory, 14 Almeida Ave., East Providence, R.I. 02914 USA.

5.8 cm (OD) circular plastic Petri dish.

60 cc disposable syringe, commercially available from Becton Dickenson, Rutherford, N.Y. USA.

Tygon tubing, size 16 with 0.12 inch inner, part number 6409-16, ⅛ inch hose barb size, commercially available as part number 6409-16 from Cole-Parmer Instrument Company, Chicago, Ill. 60648 USA.

Clear circular (5.6 cm diameter) acrylic plate to fit inside the Petri dish with one hole drilled therethrough and located approximately in the center for insertion of the Tygon tubing, and a second hole drilled therethrough for insertion of an electrode. The weight of the acrylic plate is approximately 24.9 g.

Two pieces of ¹⁄₆₄ inch platinum wire to serve as electrodes.

Figure 18:
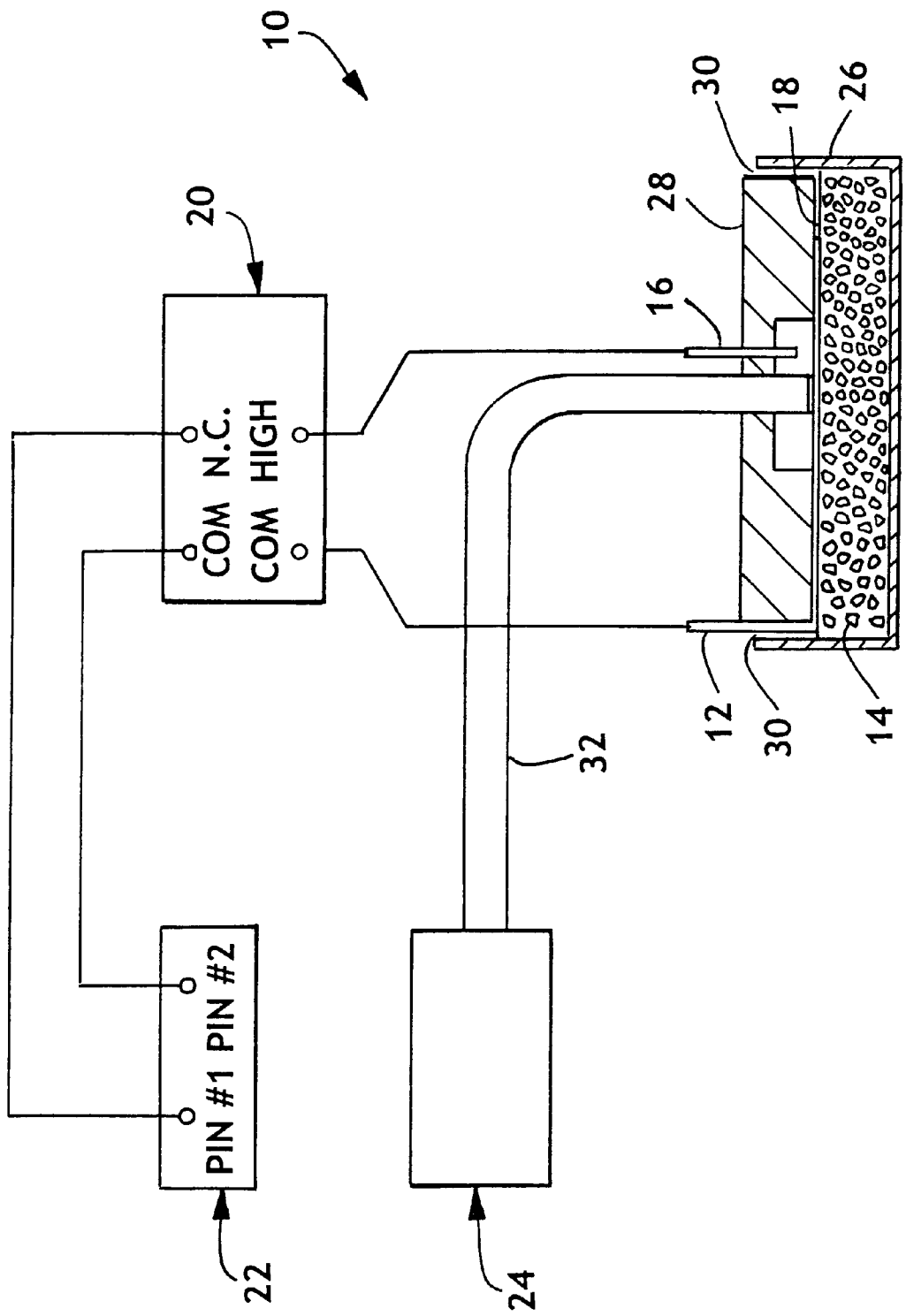
FIG. 18 illustrates an apparatus useful for conducting the On Demand Intake Test.

In FIG. 18, an apparatus (10) is illustrated that is suitable for conducting the ODI Test. During the ODI Test, a first electrode (12) remains in communication with the fluid being absorbed by the sample of absorbent material (14). A second electrode (16) is in communication with the fluid whenever an accumulation of fluid, such as a puddle, is formed on the upper surface (18) of the sample of absorbent material (14). Once a current is circulated between the first and second electrodes (i.e., when fluid has accumulated on the sample), the relay switch (20) opens, sending a 0 to 5 V raising signal to the TTL Connector (22) on the back of the Harvard Apparatus Programmable Syringe Pump (24) ("pump"). The opening of the relay switch (20) causes the cessation of fluid flow to the sample of absorbent material (14). When the first and second electrodes (12, 16) become disconnected (i.e., when there is no fluid accumulated on the sample) the relay switch (20) closes, and a 5 to 0 V lowering signal is sent to the TTL Connector (22). The closing of the relay switch (20) causes fluid to flow to the sample of absorbent material (14). The purpose of the relay switch (20) between the first and second electrodes (12, 16) and the TTL Connector (22) is to provide a clean square raising or lowering signal that triggers the fluid delivery operation of the pump (24).

Still referring to FIG. 18, a measured weight or volume of a sample of absorbent material (14) is placed in the Petri dish (26). The sample of absorbent material (14) being tested is evenly spread on the Petri dish (26). The first electrode (12) is placed on the upper surface (18) of the sample of absorbent material (14) under the acrylic plate (28). The second electrode (16) is placed approximately 2 mm above the upper surface (18) of the sample of absorbent material (14). The Tygon tubing (32) should be in contact with the upper surface (18) of the sample of absorbent material (14). Generally, the fluid is insulted at a rate of 400 mL/h onto the center of the upper surface (18) of the sample of absorbent material (14). However, the flow rate can be selected by the operator. Once the pump (24) is started, the PC (not shown) records the sequence of events. When an accumulation of fluid is detected on the upper surface (18) of the sample of absorbent material (14) by the first and second electrodes (12, 16), the pump (24) ceases delivery of the fluid. Once the accumulation of fluid has dissipated (i.e., been absorbed), the pump (24) resumes delivering fluid. The time and volume are recorded every second that the pump (24) is delivering fluid. Thus, the spaces between the points on any resulting graph are indicative of the amount of time it takes for the fluid to be absorbed by the sample of absorbent material (14). The test is stopped when the sample of absorbent material (14) is saturated with fluid. Saturation is deemed to have occurred when the pump (24) is stopped for a period longer than ten minutes or when fluid flows into the void area (30) between the Petri dish (26) and the acrylic plate (28).

Gel Bed Permeability Test Method

Figure 20:
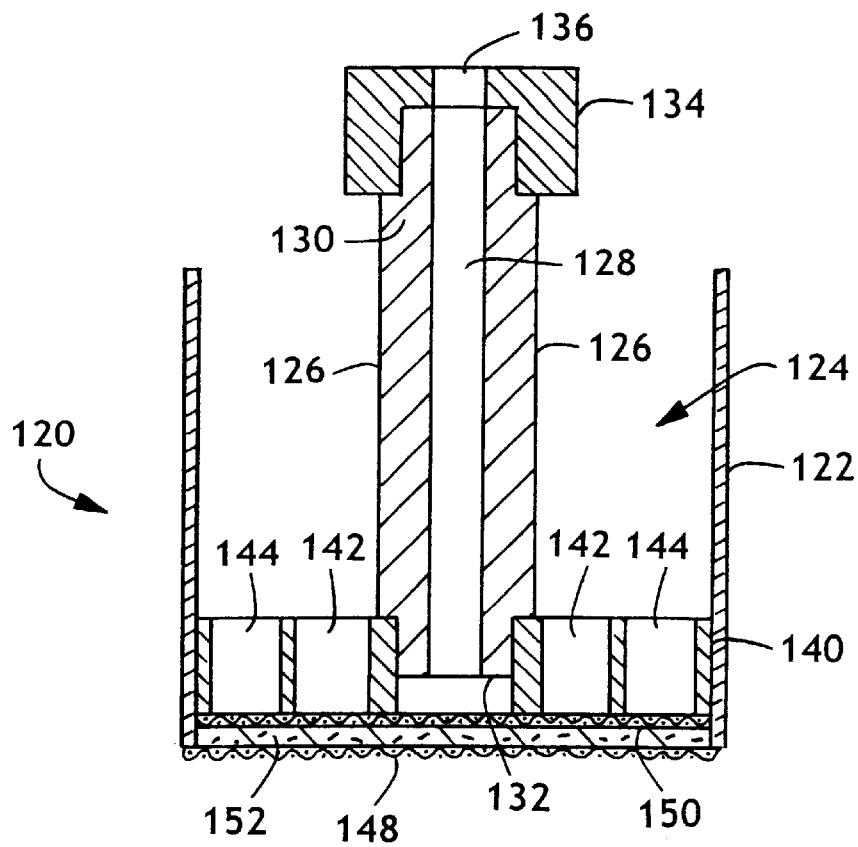
FIG. 20 illustrates an apparatus used suitable for measuring Gel Bed Permeability.
Figure 21:
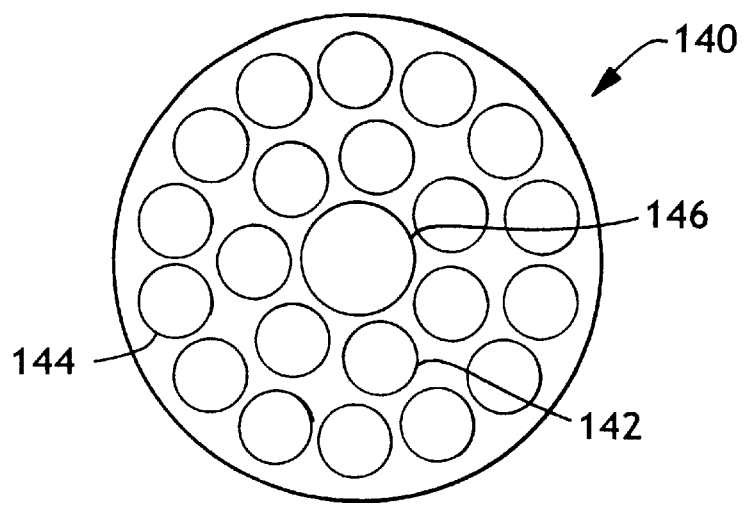
FIG. 21 illustrates a bottom plan view of the apparatus illustrated in FIG. 20.

A suitable piston/cylinder apparatus for performing the Gel Bed Permeability (GBP) test is shown in FIGS. 20 and 21. Referring to FIG. 20, an apparatus (120) consists of a cylinder (122) and a piston (generally indicated as 124). As shown in FIG. 20, the piston (124) consists of a cylindrical LEXAN® shaft (126) having a concentric cylindrical hole (128) bored down the longitudinal axis of the shaft. Both ends of the shaft (126) are machined to provide first and second ends (130, 132). A weight (134) rests on the first end (130) and has a cylindrical hole (136) bored through the center thereof. Inserted on the second end (132) is a circular piston head (140). The piston head (140) is sized so as to vertically move inside the cylinder (122). As shown in FIG. 21, the piston head (140) is provided with inner and outer concentric rings containing seven and fourteen approximately 0.375 inch (0.95 cm) cylindrical holes, respectively (indicated generally by arrows 142 and 144). The holes in each of these concentric rings are bored from the top to bottom of the piston head (140). The piston head (140) also has a cylindrical hole (146) bored in the center thereof to receive the second end (132) of the shaft (126).

Attached to the bottom end of the cylinder (122) is a No. 400 mesh stainless steel cloth screen (148) that is biaxially stretched to tautness prior to attachment. Attached to the bottom end of the piston head (140) is a No. 400 mesh stainless steel cloth screen (150) that is biaxially stretched to tautness prior to attachment. A sample of adsorbent material (152) is supported on the screen (148).

The cylinder (122) is bored from a transparent LEXAN® rod or equivalent and has an inner diameter of 6.00 cm (area=28.27 cm²), a wall thickness of approximately 0.5 cm, and a height of approximately 5.0 cm. The piston head (140) is machined from a LEXAN® rod. It has a height of approximately 0.625 inches (1.59 cm) and a diameter sized such that it fits within the cylinder (122) with minimum wall clearances, but still slides freely. A hole (146) in the center of the piston head (140) has a threaded 0.625 inch (1.59 cm) opening (18 threads/inch) for the second end (132) of the shaft (126). The shaft (126) is machined from a LEXAN® rod and has an outer diameter of 0.875 inches (2.22 cm) and an inner diameter of 0.250 inches (0.64 cm). The second end (132) is approximately 0.5 inches (1.27 cm) long and is threaded to match the hole (146) in the piston head (140). The first end (130) is approximately 1 inch (2.54 cm) long and 0.623 inches (1.58 cm) in diameter, forming an annular shoulder to support the stainless steel weight (134). The annular stainless steel weight (134) has an inner diameter of 0.625 inches (1.59 cm), so that it slips onto the first end (130) of the shaft (126) and rests on the annular shoulder formed therein. The combined weight of the piston (124) and the weight (134) equals approximately 596 g, which corresponds to a pressure of 0.30 psi (20,685 dynes/cm²), for an area of 28.27 cm².

When fluids flow through the piston/cylinder apparatus, the cylinder (122) generally rests on a 16-mesh, rigid stainless-steel support screen (not shown) or equivalent.

The piston and weight are placed in an empty cylinder to obtain a measurement from the bottom of the weight to the top of the cylinder. This measurement is taken using a caliper readable to 0.01 mm. This measurement will later be used to calculate the height of the bed of the sample of adsorbent material (152). It is important to measure each cylinder empty and keep track of which piston and weight were used. The same piston and weight should be used for measurement when the sample of adsorbent material is swollen.

The adsorbent layer used for GBP measurements is formed by swelling approximately 0.9 g of a sample of adsorbent material in the GBP cylinder apparatus (dry adsorbent material should be spread evenly over the screen of the cylinder prior to swelling) with a fluid, typically 0.9% (w/v) aqueous NaCl, for a time period of approximately 15 minutes. The sample of adsorbent material is taken from a population of adsorbent material that is prescreened through US standard 30 mesh and retained on US standard 50 mesh. The adsorbent material, therefore, has a particle size of between 300 and 600 microns. The particles may be pre-screened by hand or automatically prescreened with, for example, a Ro-Tap Mechanical Sieve Shaker Model B, commercially available from W. S. Tyler, Inc., Mentor, Ohio USA.

At the end of the 15 minute period, the cylinder is removed from the fluid and the piston/weight assembly is placed on the sample of adsorbent material. The thickness of the swollen sample of adsorbent material is determined by measuring from the bottom of the weight to top of the cylinder with a micrometer. The value obtained when taking this measurement with the empty cylinder is subtracted from the value obtained after swelling the sample of adsorbent material. The resulting value is the height of the bed of the swollen sample of adsorbent material, H.

The GBP measurement is initiated by adding the fluid to the cylinder (122) until the fluid attains a height of 4.0 cm above the bottom of the sample of adsorbent material (152). This fluid height is maintained throughout the test. The quantity of fluid passing through the sample of adsorbent material (152) versus time is measured gravimetrically. Data points are collected every second for the first two minutes of the test and every two seconds for the remainder. When the data are plotted as quantity of fluid passing through the bed of the sample of adsorbent material versus time, it becomes clear to one skilled in the art when a steady flow rate has been attained. Only data collected once the flow rate has become steady is used in the flow rate calculation. The flow rate, Q, through the sample of adsorbent material (152), is determined in units of g/s by a linear least-square fit of fluid passing through the sample of adsorbent material (in grams) versus time (in seconds).

Permeability in cm² is obtained by the following equation:

$$K=[Q*(H*Mu)]/[A*Rho*P]$$

Where K=Gel Bed Permeability (cm²); Q=flow rate (g/sec); H=height of bed of sample of adsorbent material (cm); Mu=liquid viscosity (poise); A=cross-sectional area for liquid flow (cm²); Rho=liquid density (g/cm³); and P=hydrostatic pressure (dynes/cm²) (normally approximately 3,923 dynes/cm²).

EXAMPLES

The following Examples describe various embodiments of the invention. Other embodiments within the scope of the claims herein will be apparent to one skilled in the art from consideration of the specification or practice of the invention as disclosed herein. It is intended that the specification, together with the Examples, be considered exemplary only, with the scope and spirit of the invention being indicated by the claims which follow the Examples.

Example 1

The superabsorbent material utilized in this Example was Favor SXM 880, a polyacrylate superabsorbent material commercially available from Stockhausen, Inc., Greensboro, N.C. USA. The coating material of this Example was Avicel 101, a microcrystalline cellulose powder commercially available from FMC Corporation, Philadelphia, Pa. USA. The superabsorbent-containing composite of this Example, Favor SXM 880 covered with Avicel 101, was prepared at The Coating Place, Verona, Wis. USA, using an embodiment of the process described herein. The association agent utilized was distilled water. The superabsorbent material, the coating material and the association agent were added in equal parts, by weight. The process provided for the addition of 1 part Avicel 101 to a fluidized bed coating apparatus. While the Avicel 101 was being fluidized, the 1 part distilled water was added to the process. After the distilled water was added, the 1 part Favor SXM 880 was added to the process. Fluidizing was continued as the temperature was raised. When the air outlet temperature equaled approximately 88° C., the run was considered complete and the superabsorbent-containing composite was bagged. The superabsorbent-containing composite prepared according to this Example was later sieved to remove particles less than 50 mesh (Tyler equivalent). Chemical analysis of the superabsorbent-containing composite indicated that it had a superabsorbent material to coating material ratio of about 69:31, by weight.

A sample of the superabsorbent-containing composite (Sample A) of this Example was compared to uncoated (i.e., a superabsorbent material that is not coated with the coating material of the present invention) or standard Favor SXM 880 (Sample B) for absorbency rate and rewet. The results of this comparison are provided in Table 1, which follows:

TABLE 1

|  | Sample A | Sample B |
| --- | --- | --- |
| Insult 1 (s) | 35.0 | 49.8 |
| Insult 2 (s) | 38.0 | 188.0 |
| Insult 3 (s) | 18.8 | 57.5 |
| Rewet (g) | 0.1 | 0.2 |
| Insult 1 (s) | 37.7 | 300+ |
| Insult 2 (s) | 37.9 | |
| Insult 3 (s) | 39.3 | |
| Rewet (g) | 0.1 | |
| Insult 1 (s) | 54.4 | |
| Insult 2 (s) | 114.6 | |
| Insult 3(s) | 212.1 | |
| Rewet (g) | 0.2 | |
| Insult 1 (s) | 300+ | |

The superabsorbent-containing composite of Sample A increased the absorbency rate versus the uncoated superabsorbent material of Sample B at every measurement point and substantially increased the amount of simulant which could be absorbed before gel blocking occurred. The coating material also increased the efficacy and utilization of the superabsorbent material in the handling of a complex fluid. The term "gel blocking" refers to the situation wherein blockage occurs within the interstitial spaces between the particles, or between the particles and the fibers, if in a fibrous absorbent core of a disposable absorbent article, thus preventing the flow of fluid through the interstitial spaces.

The CFRC for Sample A was calculated to be at least about 18.4 g/g, while the CFRC for Sample B was calculated to be about 15.9 g/g.

Example 2

This Example illustrates that the present invention is not limited to a single superabsorbent or a single process. The superabsorbent material utilized in this Example was DRYTECH® 2035, a superabsorbent material commercially available from Dow Chemical Company, Midland, Mich. USA. The coating material of this Example was Avicel 101, a microcrystalline cellulose powder commercially available from FMC Corporation, Philadelphia, Pa. USA. The superabsorbent-containing composite of this Example, DRYTECH® 2035 covered with Avicel 101, was prepared at The Coating Place, Verona, Wis. USA, using an embodiment of the process described herein. The association agent utilized was distilled water. The superabsorbent material, the coating material and the association agent were added in parts having a ratio of about 1:1:2, by weight. The process provided for the addition of 1 part Avicel 101 to a fluidized bed coating apparatus. While the Avicel 101 was being fluidized, the 1 part DRYTECH® 2035 was added to the process. After the DRYTECH® 2035 was added, the 2 parts distilled water were added to the process. Fluidizing was continued as the temperature was raised. When the air outlet temperature equaled approximately 88° C., the run was considered complete and the superabsorbent-containing composite was bagged. A run produced approximately 400 g of superabsorbent-containing composite.

A sample of the superabsorbent-containing composite (Sample C) of this Example was compared to uncoated DRYTECH® 2035 (Sample D) for absorbency rate and rewet. Sample C was tested as prepared, without sieving. The results of this comparison are provided in Table 2, which follows:

TABLE 2

|  | Sample C | Sample D |
| --- | --- | --- |
| Insult 1 (s) | 34.32 | 300+ |
| Insult 2 (s) | 49.77 |  |
| Insult 3 (s) | 36.54 |  |
| Rewet (g) | 0.621 |  |
| Insult 1 (s) | 59.81 |  |
| Insult 2 (s) | 146.1 |  |
| Insult 3 (s) | 192.2 |  |
| Rewet (g) | 1.038 |  |
| Insult 1 (s) | 300+ |  |

As in Example 1, the superabsorbent-containing composite, Sample C in this Example, increased the absorbency rate versus the uncoated superabsorbent material of Sample D. In addition, Sample C had a significant reduction in gel blocking when compared to Sample D. The coating material also increased the efficacy and utilization of the superabsorbent material in the handling of a complex fluid.

The CFRC for Sample C was calculated to be at least about 13.1 g/g, while the CFRC for Sample D was calculated to be about 19.1 g/g.

Example 3

This Example illustrates that the invention is not limited to the selection of a single cellulose powder or to a single process. The superabsorbent material utilized in this Example was Favor SXM 880, a polyacrylate superabsorbent material commercially available from Stockhausen, Inc., Greensboro, N.C. USA. The coating material of this Example was Sanacel 150, a cellulose powder commercially available from Cellulose Filler Factory, Chesterton, Md. USA. The superabsorbent-containing composite of this Example, Favor SXM 880 covered with Sanacel 150, was prepared at The Coating Place, Verona, Wis. USA, using an embodiment of the process described herein. The association agent utilized was distilled water. The superabsorbent material, the coating material and the association agent were added in parts having a ratio of 2:1:1, by weight. The process provided for the addition of 1 part Sanacel 150 to a fluidized bed coating apparatus. While the 1 part Sanacel 150 was being fluidized, the 1 part distilled water was added to the process. After the distilled water was added, the 2 parts Favor SXM 880 were added to the process. Fluidizing was continued as the temperature was raised. When the air outlet temperature equaled approximately 88° C., the run was considered complete and the superabsorbent-containing composite was bagged. A run produced approximately 1,850 g of superabsorbent-containing composite. Chemical analysis of the superabsorbent-containing composite indicated that it had a superabsorbent material to coating material ratio of approximately 69:31, by weight.

A sample of the superabsorbent-containing composite (Sample E) of this Example was compared to uncoated Favor SXM 880 (Sample B) for absorbency rate and rewet. The results of this comparison are provided in Table 3, which follows:

TABLE 3

|  | Sample E | Sample B |
| --- | --- | --- |
| Insult 1 (s) | 32.9 | 49.8 |
| Insult 2 (s) | 49.3 | 188.0 |
| Insult 3 (s) | 57.2 | 57.5 |
| Rewet (g) | 0.3 | 0.2 |
| Insult 1 (s) | 45.8 | 300+ |
| Insult 2 (s) | 58.7 |  |
| Insult 3 (s) | 175.3 |  |
| Rewet (g) | 0.2 |  |
| Insult 1 (s) | 300+ |  |

The Retention Capacity for Sample E was calculated to be at least about 19.6 g/g Example 4

This Example illustrates that coating materials are not limited to cellulose materials. The superabsorbent material utilized in this Example was Favor SXM 880, a polyacrylate superabsorbent material commercially available from Stockhausen, Inc., Greensboro, N.C. USA. The coating material of this Example was vermiculite, a soil conditioner commercially available from Scotts Company, Marysville, Ohio USA. The superabsorbent-containing composite of this Example, Favor SXM 880 covered with vermiculite, was prepared at The Coating Place, Verona, Wis. USA, using an embodiment of the process described herein. The association agent utilized was distilled water. The superabsorbent material, the coating material and the association agent were added in equal parts, by weight. The process provided for the addition of the 1 part vermiculite to a fluidized bed coating apparatus. While the 1 part vermiculite was being fluidized, the 1 part distilled water was added to the process. After the distilled water was added, the 1 part Favor SXM 880 was added to the process. Fluidizing was continued as the temperature was raised. When the air outlet temperature equaled approximately 88° C., the run was considered complete and the superabsorbent-containing composite was bagged. A run produced approximately 344 g of superabsorbent-containing composite.

A sample of the superabsorbent-containing composite (Sample F) of this Example was compared to uncoated Favor SXM 880 (Sample B) for absorbency rate and rewet. The results of this comparison are provided in Table 4, which follows:

TABLE 4

|  | Sample F | Sample B |
| --- | --- | --- |
| Insult 1 (s) | 32.6 | 49.8 |
| Insult 2 (s) | 36.1 | 188.0 |
| Insult 3 (s) | 19.9 | 57.5 |
| Rewet (g) | 0.3 | 0.2 |
| Insult 1 (s) | 50.2 | 300+ |
| Insult 2 (s) | 73.0 |  |
| Insult 3 (s) | 61.0 |  |
| Rewet (g) | 0.7 |  |
| Insult 1 (s) | 193.1 |  |
| Insult 2 (s) | 182.5 |  |
| Insult 3 (s) | 156.3 |  |
| Rewet (g) | 1.2 |  |
| Insult 1 (s) | 300+ |  |

The CFRC for Sample F was calculated to be at least about 14.9 g/g.

Example 5

This Example illustrates that the association agent can include more than one material. The superabsorbent material utilized in this Example was DRYTECH® 2035, a superabsorbent material commercially available from Dow Chemical Company, Midland, Mich. USA. The coating material of this Example was Avicel 101, a microcrystalline cellulose powder commercially available from FMC Corporation, Philadelphia, Pa. USA. The association agent included non-fat dry milk, CARNATION® brand, commercially available from Nestle Corporation. The superabsorbent-containing composite of this Example, DRYTECH® 2035 covered with Avicel 101, was prepared at The Coating Place, Verona, Wis. USA, using an embodiment of the process described herein. The association agent utilized was an aqueous solution of non-fat dry milk having a distilled water to non-fat dry milk ratio of approximately 4:1, by weight. The superabsorbent material, the coating material and the association agent were added in parts having a ratio of approximately 1:1:2, by weight. The process provided for the addition of the 1 part Avicel 101 to a fluidized bed coating apparatus. While the Avicel 101 was being fluidized, the 1 part DRYTECH® 2035 was added to the process. After the DRYTECH® 2035 was added, the 2 parts association agent were added to the process. Fluidizing was continued as the temperature was raised. When the air outlet temperature equaled approximately 88° C., the run was considered complete and the superabsorbent-containing composite was bagged. A run produced approximately 484 g of superabsorbent-containing composite.

A sample of the superabsorbent-containing composite (Sample G) of this Example was compared to a superabsorbent-containing composite including DRYTECH® 2035 substantially covered with Avicel 101 (Sample C) for absorbency rate and rewet. Sample G was tested as prepared, without sieving. The results of this comparison are provided in Table 5, which follows:

TABLE 5

|  | Sample G | Sample C |
| --- | --- | --- |
| Insult 1 (s) | 36.6 | 34.32 |
| Insult 2 (s) | 45.3 | 49.77 |
| Insult 3 (s) | 21.0 | 36.54 |
| Rewet (g) | 0.5 | 0.6 |
| Insult 1 (s) | 60.9 | 59.81 |
| Insult 2 (s) | 103.7 | 146.1 |
| Insult 3 (s) | 84.9 | 192.2 |
| Rewet (g) | 0.7 | 1.0 |
| Insult 1 (s) | 139.8 | 300+ |
| Insult 2 (s) | 300+ |  |

This Example further illustrates that the presence of the non-fat dry milk improves the absorbency rate and increases the efficacy and utilization (i.e., reduces gel blocking) of Sample G when compared to Sample C, which solely utilized distilled water as an association agent.

Example 6

This Example illustrates that aqueous solutions of association agent can be used with coating materials other than cellulose. The superabsorbent material utilized in this Example was DRYTECH® 2035, a superabsorbent material commercially available from Dow Chemical Company, Midland, Mich. USA. The coating material of this Example was Zeofree 5175B, a granulated, precipitated silica commercially available from J. M. Huber, Havre de Grace, Md. USA. The association agent included non-fat dry milk, CARNATION® brand, commercially available from Nestle Corporation. The superabsorbent-containing composite of this Example, DRYTECH® 2035 covered with Avicel 101, was prepared at The Coating Place, Verona, Wis. USA, using an embodiment of the process described herein. The association agent utilized was an aqueous solution of non-fat dry milk having a distilled water to non-fat dry milk ratio of approximately 4:1, by weight. The process provided for the addition of 200 g of Zeofree 5175B and 280 g of DRYTECH® 2035 to a fluidized bed coating apparatus. While the Zeofree 5175B and DRYTECH® 2035 were being fluidized, 480 g of the association agent were added to the process. Fluidizing was continued as the temperature was raised. When the air outlet temperature equaled approximately 88° C., the run was considered complete and the superabsorbent-containing composite was bagged. A run produced approximately 528 g of superabsorbent-containing composite.

A sample of the superabsorbent-containing composite (Sample H) of this Example was compared to Sample G for absorbency rate and rewet. Sample H was tested as prepared, without sieving. The results of this comparison are provided in Table 6, which follows:

TABLE 6

|  | Sample H | Sample G |
|---|---|---|
| Insult 1 (s) | 34.3 | 36.6 |
| Insult 2 (s) | 56.3 | 45.3 |
| Insult 3 (s) | 21.0 | 21.0 |
| Rewet (g) | 0.4 | 0.5 |
| Insult 1 (s) | 74.8 | 60.9 |
| Insult 2 (s) | 65.1 | 103.7 |
| Insult 3 (s) | 74.5 | 84.9 |
| Rewet (g) | 0.7 | 0.7 |
| Insult 1 (s) | 123.9 | 139.8 |
| Insult 2 (s) | 152.3 | |
| Insult 3 (s) | 46.0 | |
| Rewet (g) | 0.9 | |
| Insult 1 (s) | 90.2 | |
| Insult 2 (s) | 245.8 | |
| Insult 3 (s) | 300+ | |

This Example further illustrates that the presence of the non-fat dry milk in combination with Zeofree 5175B improves the absorbency rate and increases the efficacy and utilization (i.e., reduces gel blocking) of Sample H, over at least Samples G, D and C, in the handling of a complex fluid.

The CFRC for Sample H was calculated to be at least about 12.2 g/g.

Example 7

This Example further illustrates the effect that can be achieved through selection of coating materials, both soluble and insoluble in water. The superabsorbent material utilized in this Example was DRYTECH® 2035, a superabsorbent material commercially available from Dow Chemical Company, Midland, Mich. USA. The coating materials of this Example were Zeofree 5175B, a granulated, precipitated silica commercially available from J. M. Huber, Havre de Grace, Md. USA, and TWEEN® 20, an ethoxylated polysorbate available from ICI Surfactants, Wilmington, Del. USA. The association agent utilized was distilled water. The TWEEN® 20 was dissolved in distilled water to make a 20 percent by weight solution. The superabsorbent-containing composite of this Example, DRYTECH® 2035 covered with TWEEN® 20 and Zeofree 5175B, was prepared at The Coating Place, Verona, Wis. USA, using an embodiment of the process described herein. The process provided for the addition of approximately 126 g of Zeofree 5175B and 200 g of DRYTECH® 2035 to a fluidized bed coating apparatus. While the Zeofree 5175B and DRYTECH® 2035 were being fluidized, approximately 326 g of the 20 percent TWEEN® 20 solution were added to the process. Fluidizing was continued as the temperature was raised. When the air outlet temperature equaled approximately 88° C., the run was considered complete and the superabsorbent-containing composite was bagged. A run produced approximately 392 g of superabsorbent-containing composite.

A sample of the superabsorbent-containing composite (Sample I) of this Example was compared to Sample H for absorbency rate and rewet. Sample I was tested as prepared, without sieving. The results of this comparison are provided in Table 7, which follows:

TABLE 7

|  | Sample I | Sample H |
|---|---|---|
| Insult 1 (s) | 54.29 | 34.3 |
| Insult 2 (s) | 68.98 | 56.3 |
| Insult 3 (s) | 38.57 | 21.0 |
| Rewet (g) | 0.504 | 0.4 |
| Insult (s) | 37.77 | 74.8 |
| Insult 2 (s) | 41.86 | 65.1 |
| Insult 3 (s) | 18.92 | 74.5 |
| Rewet (g) | 0.61 | 0.7 |
| Insult 1 (s) | 50.77 | 123.9 |
| Insult 2 (s) | 50.34 | 152.3 |
| Insult 3 (s) | 92.2 | 46.0 |
| Rewet (g) | 0.824 | 0.9 |
| Insult 1 (s) | 75.38 | 90.2 |
| Insult 2 (s) | 87.68 | 245.8 |
| Insult 3 (s) | 181.8 | 300+ |
| Rewet (g) | NA | |
| Insult 1 (s) | 205.7 | |
| Insult 2 (s) | 300+ | |

Example 8

This Example illustrates results using the ODI Test Method. The ODI Test was performed using four fluids: saline, plasma, blood and simulant. For all tests, there were five grams of the sample of absorbent material. The superabsorbent material utilized in this Example was Favor SXM 880, a polyacrylate superabsorbent material commercially available from Stockhausen, Inc., Greensboro, N.C. USA. The coating material of this Example was Avicel 101, a microcrystalline cellulose powder commercially available from FMC Corporation, Philadelphia, Pa. USA. The superabsorbent-containing composite of this Example, Favor SXM 880 covered with Avicel 101, was prepared at The Coating Place, Verona, Wis. USA, using an embodiment of the process described herein. The association agent utilized was distilled water. The superabsorbent material, the coating material and the association agent were added in equal parts, by weight. The process provided for the addition of the 1 part Avicel 101 to a fluidized bed coating apparatus. While the Avicel 101 was being fluidized, the 1 part distilled water was added to the process. After the distilled water was added, the 1 part Favor SXM 880 was added to the process. Fluidizing was continued as the temperature was raised. When the air outlet temperature equaled approximately 88° C., the run was considered complete and the superabsorbent-containing composite was bagged. The superabsorbent-containing composite prepared according to this Example was later sieved to remove particles less than 50 mesh (Tyler equivalent), which it is believed were principally unattached cellulose powder. Chemical analysis of the superabsorbent-containing composite indicated that it had a superabsorbent material to coating material ratio of about 69:31, by weight. For consistency, the standard or uncoated Favor SXM 880 was also sieved through a 50 mesh.

For saline, both the uncoated superabsorbent material and the superabsorbent-containing composite exhibited approximately the same absorption curve. For the three other fluids tested, the superabsorbent-containing composite absorbs a greater quantity of fluid at a faster rate and over a longer period of time that the uncoated superabsorbent material. The difference between the absorbency rate of the superabsorbent-containing composite and the absorbency rate of its corresponding uncoated superabsorbent material increases as the fluid becomes more complex, i.e., the difference between the absorbency rate of the superabsorbent-containing composite and the absorbency rate of its corresponding uncoated superabsorbent material for blood is larger than it is for plasma, and larger for simulant than for blood. As the fluid becomes more complex, however, the absorption capacity of both the superabsorbent-containing composite and its corresponding uncoated superabsorbent material decreases. For the superabsorbent-containing composite, the three fluids other than saline are absorbed substantially instantaneously (i.e., flow rate 400 mL/h) up to 15 mL, then intake slows. A substantial portion of the superabsorbent-containing composite has been immersed with fluid by the end of the test. For the uncoated superabsorbent material, however, gel blocking occurs relatively quickly for blood and simulant. This is evidenced by the fluid flow being stopped when build-up occurs. Moreover, it is common for the uncoated superabsorbent material at the bottom of the Petri dish to not come into contact with the fluid due to gel blocking.

The foregoing ODI Test results are graphically depicted in FIGS. 14 through 16 and illustrate that the superabsorbent-containing composites of the present invention offer a number of advantages including a reduction in gel blocking and an improved wicking of complex fluids such as protein (plasma), red blood cells (blood) and mucins (simulant).

Example 9

Figure 19:
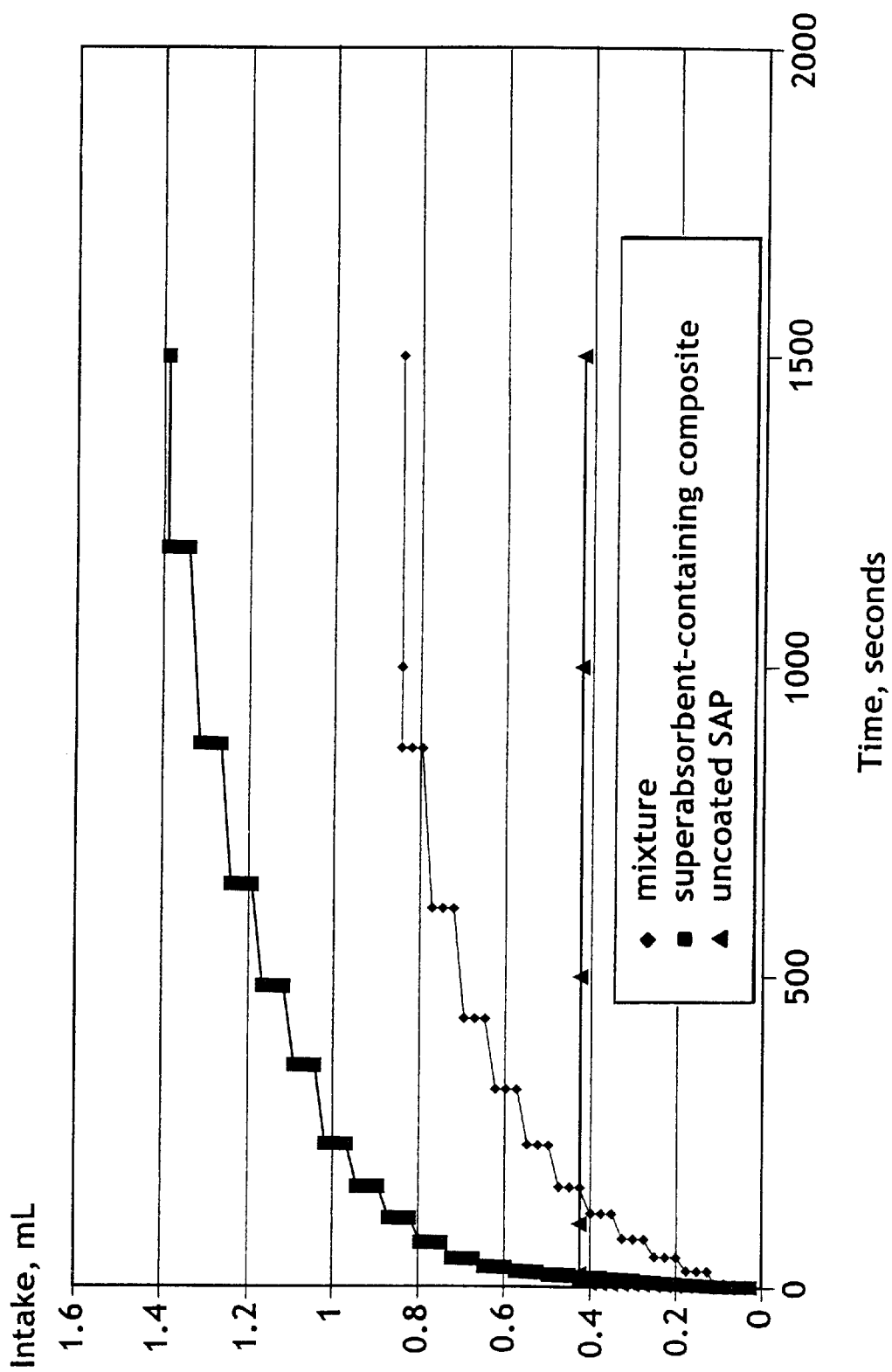
FIG. 19 illustrates a plot of the data obtained in Example 9 herein.

This Example serves to illustrate the improved intake of complex fluids demonstrated by superabsorbent-containing composites of the present invention when compared to a mixture of superabsorbent material and coating material prepared as described herein. The superabsorbent material utilized in this Example was Favor SXM 880, a polyacrylate superabsorbent material commercially available from Stockhausen, Inc. Greensboro, N.C. USA. The coating material of this Example was EXCEL 110, a cellulose powder commercially available from Functional Foods, Elizabethtown, N.J. USA. The superabsorbent-containing composite of this Example, Favor SXM 880 covered with EXCEL 110, was prepared at The Coating Place, Verona, Wis. USA, using an embodiment of the process described herein. The association agent utilized was distilled water. The superabsorbent material, the coating material and the association agent were added in parts having a ratio of 2:1:1, by weight. The process provided for the addition of 1 part EXCEL 110 to a fluidized bed coating apparatus. While the 1 part EXCEL 110 was being fluidized, the 1 part distilled water was added to the process. After the distilled water was added, the 2 parts Favor SXM 880 were added to the process. Fluidizing was continued as the temperature was raised. When the air outlet temperature equaled approximately 44° C., the run was considered complete and the superabsorbent-containing composite was bagged. The mixture of superabsorbent material and coating material was prepared by placing 2 parts Favor SXM 880 and 1 part EXCEL 110 into a Hobart blender and gently mixing until a generally uniform mixture of both the Favor SXM 880 and EXCEL 110 was obtained. Thereafter, the ODI Test was conducted on samples of the superabsorbent-containing composite, the mixture and a standard superabsorbent material (in this instance, Favor SXM 880, and identified in FIG. 19 as uncoated SAP). The fluid used in this Example was defibrinated swine blood adjusted at approximately 33% hematocrit, commercially available from Cocalico Biologicals, Inc., 449 Stevens Rd., P.O. Box 265, Reamstown, Pa. 17567 USA. The results of this Example are graphically illustrated in FIG. 19.

Example 10

This Example serves to illustrate the effect that different coating materials have on the permeability of the superabsorbent-containing composites of the present invention. The superabsorbent material utilized in this Example was either DRYTECH® 2035, a superabsorbent material commercially available from Dow Chemical Company, Midland, Mich. USA, or Favor SXM 880, a polyacrylate superabsorbent material commercially available from Stockhausen, Inc. Greensboro, N.C. USA. The coating material of this Example was either EXCEL 110, a cellulose powder commercially available from Functional Foods, Elizabethtown, N.J. USA, Zeofree 5175A, a granulated, precipitated silica commercially available from J. M. Huber, Havre de Grace, Md. USA, or combinations or EXCEL 110 and Zeofree 5175A. The superabsorbent-containing composites of this Example were prepared at The Coating Place, Verona, Wis. USA, using an embodiment of the process described herein. The association agent utilized was distilled water. The superabsorbent material, the coating material(s) and the association agent were added in the amounts indicated in Table 8. The process provided for the addition of the coating material(s) to a fluidized bed coating apparatus. While the coating material(s) was (were) being fluidized, the association agent was added to the process. After the association agent was added, the superabsorbent material was added to the process. For the samples identified in Table 8, fluidizing was continued as the temperature was elevated. When the air outlet temperature equaled approximately 44° C., the run was considered complete. Gel Bed Permeability was determined using the Gel Bed Permeability Test Method described above.

TABLE 8

| | Coating Material | | Associ- | Superabsorbent Material | | |
|---|---|---|---|---|---|---|
| Sample ID | Excel 110 (g) | Zeofree 5175A (g) | ation Agent (g) | Favor SXM 880 (g) | Drytech 2035 (g) | Gel Bed Permeability (cm$^2$) |
| 10-4 | 500 | — | 500 | 1,000 | — | 165.96 |
| 10-5 | 500 | 100 | 600 | 500 | — | 414.08 |
| 10-6 | 500 | 100 | 600 | 1,000 | — | 475.18 |
| 10-7 | 300 | 300 | 600 | 1,000 | — | 1,504.37 |
| 10-8 | 100 | 500 | 600 | 1,000 | — | 1,296.49 |
| 10-12 | 500 | — | 500 | — | 1,000 | 260.12 |
| 10-13 | 500 | — | 560 | — | 1,500 | 163.28 |
| 10-14 | 500 | 100 | 600 | — | 1,000 | 447.00 |
| 10-15 | 300 | 300 | 600 | — | 1,000 | 531.88 |
| 10-16 | 100 | 500 | 600 | — | 1,000 | 2,009.54 |

For the samples identified in Table 9, the steps for preparation were the same as the foregoing samples in this Example except that after the superabsorbent material was added to the process, fluidizing was continued at an outlet temperature approximating that of the inlet temperature (i.e., room temperature). Gel Bed Permeability was determined using the Gel Bed Permeability Test Method described above.

TABLE 9

| | Coating Material | | Superabsorbent Material | | | |
|---|---|---|---|---|---|---|
| Sample ID | Excel 110 (g) | Zeofree 5175A (g) | Association Agent (g) | Favor SXM 880 (g) | Drytech 2035 (g) | Gel Bed Permeability (cm²) |
| 10-1 | 500 | — | 500 | 1,000 | — | 133.53 |
| 10-2 | 250 | — | 250 | 1,000 | — | 114.62 |
| 10-3 | 125 | — | 125 | 1,000 | — | 109.69 |
| 10-9 | 500 | — | 500 | — | 1,000 | 538.20 |
| 10-10 | 500 | — | 250 | — | 1,000 | 197.18 |
| 10-11 | 500 | — | 125 | — | 1,000 | 79.95 |

As indicated herein, the Gel Bed Permeability of the superabsorbent-containing composites of the present invention desirably ranges between about 80 to greater than about 2,000 cm².

In view of the above, it will be seen that the several advantages of the invention are achieved and other advantageous results attained.

As various changes could be made in the above processes and composites without departing from the scope of the invention, it is intended that all matter contained in the above description and shown in the accompanying drawings shall be interpreted as illustrative and not in a limiting sense.

What is claimed is:

1. A superabsorbent-containing composite comprising at least one particle of a stiff-gelling superabsorbent material covered with at least a first layer of at least one particle of at least one coating material, the first layer of the coating material being in intimate association with and covering the surface of the superabsorbent material, the superabsorbent material being capable of selectively removing at least a portion of an amount of at least one specific component of a complex fluid and the coating material being capable of selectively removing at least a portion of an amount of at least one other specific component of the complex fluid.

2. The composite of claim 1, wherein the intimate association of the coating material with the superabsorbent material is achieved with the use of an association agent.

3. The composite of claim 1, wherein the coating material comprises a hydrophilic material.

4. The composite of claim 3, wherein the coating material comprises a cellulosic material.

5. The composite of claim 1, wherein the coating material comprises a silicate.

6. The composite of claim 5, wherein the coating material is selected from the group consisting of precipitated silica, fumed silica, silicon dioxide, zeolites, clays, vermiculite, perlite and mixtures thereof.

7. The composite of claim 1, wherein the coating material comprises insoluble proteins.

8. The composite of claim 7, wherein the coating material is selected from among the group consisting of zein, texturized vegetable proteins and mixtures thereof.

9. The composite of claim 7, wherein the coating material comprises soy protein.

10. The composite of claim 2, wherein the association agent is selected from the group consisting of water, volatile organic solvents, aqueous solutions of film-forming materials, synthetic adhesives and mixtures thereof.

11. The composite of claim 2, wherein the association agent is selected from the group consisting of water, dried milk, lactose, soy protein, casein, polyvinyl alcohol and mixtures thereof.

12. The composite of claim 2, wherein the association agent comprises water and dried milk.

13. The composite of claim 2, wherein the association agent comprises water.

14. The composite of claim 1, wherein the superabsorbent-containing composite has a complex fluid retention capacity of between 0 and about 20 g/g.

15. The composite of claim 1, wherein the superabsorbent-containing composite has a complex fluid retention capacity of at least about 13 g/g.

16. A superabsorbent-containing composite comprising at least one particle of a stiff-gelling superabsorbent material covered with at least a first layer of at least one particle of at least one coating material, the first layer of the coating material being in intimate association with and covering the surface of the superabsorbent material, the superabsorbent material being capable of selectively removing at least a portion of an amount of at least one specific component of a complex fluid and the coating material being capable of selectively removing at least a portion of an amount of at least one specific component of the complex fluid, wherein the coating material is chemically modified.

17. The composite of claim 16, wherein the intimate association of the coating material with the superabsorbent material is achieved with the use of an association agent.

18. The composite of claim 16, wherein the coating material is chemically modified by adsorption.

19. The composite of claim 18, wherein the coating material is chemically modified by use of a cationic debonder.

20. The composite of claim 16, wherein the coating material is chemically modified by derivatization.

21. The composite of claim 20, wherein the coating material is chemically modified by conversion to diethylamino cellulose.

22. The composite of claim 17, wherein the association agent comprises water.

23. The composite of claim 16, wherein the superabsorbent-containing composite has a complex fluid retention capacity of between 0 and about 20 g/g.

24. The composite of claim 16, wherein the superabsorbent-containing composite has a complex fluid retention capacity of at least about 13 g/g.

25. The composite of claim 16, wherein the coating material is capable of selectively removing at least a portion of an amount of at least one other specific component of the complex fluid.

26. A superabsorbent-containing composite comprising at least one particle of a stiff-gelling superabsorbent material covered with at least a first layer of at least one particle of at least one coating material, the first layer of the coating material being in intimate association with and covering the surface of the superabsorbent material, the superabsorbent material being capable of selectively removing at least a portion of an amount of at least one specific component of a complex fluid, wherein the coating material substantially inhibits those components of a complex fluid having a diameter of greater than about five microns from being adsorbed onto the surface of the superabsorbent material of the composite.

27. The composite of claim 26, wherein the intimate association of the coating material with the superabsorbent material is achieved with the use of an association agent.

28. The composite of claim 26, wherein the coating material comprises a hydrophilic material.

29. The composite of claim 28, wherein the coating material comprises a cellulosic material.

30. The composite of claim 26, wherein the coating material comprises a silicate.

31. The composite of claim 30, wherein the coating material is selected from the group consisting of precipitated silica, fumed silica, silicon dioxide, zeolites, clays, vermiculite, perlite and mixtures thereof.

32. The composite of claim 26, wherein the coating material comprises insoluble proteins.

33. The composite of claim 32, wherein the coating material is selected from among the group consisting of zein, texturized vegetable proteins and mixtures thereof.

34. The composite of claim 32, wherein the coating material comprises soy protein.

35. The composite of claim 27, wherein the association agent comprises water.

36. The composite of claim 26, wherein the superabsorbent-containing composite has a complex fluid retention capacity of between 0 and about 20 g/g.

37. The composite of claim 26, wherein the superabsorbent-containing composite has a complex fluid retention capacity of at least about 13 g/g.

38. A superabsorbent-containing composite comprising at least one particle of a stiff-gelling superabsorbent material covered with at least a first layer of at least one particle of at least one coating material, the first layer of the coating material being in intimate association with and covering the surface of the superabsorbent material, the superabsorbent material being capable of selectively removing at least a portion of an amount of at least one specific component of a complex fluid and the coating material being capable of selectively removing at least a portion of an amount of at least one specific component of the complex fluid.

39. The composite of claim 38, wherein the intimate association of the coating material with the superabsorbent material is achieved with the use of an association agent.

40. The composite of claim 38, wherein the coating material comprises a hydrophilic material.

41. The composite of claim 40, wherein the coating material comprises a cellulosic material.

42. The composite of claim 38, wherein the coating material comprises a silicate.

43. The composite of claim 42, wherein the coating material is selected from the group consisting of precipitated silica, fumed silica, silicon dioxide, zeolites, clays, vermiculite, perlite and mixtures thereof.

44. The composite of claim 38, wherein the coating material comprises insoluble proteins.

45. The composite of claim 44, wherein the coating material is selected from among the group consisting of zein, texturized vegetable proteins and mixtures thereof.

46. The composite of claim 44, wherein the coating material comprises soy protein.

47. The composite of claim 39, wherein the association agent comprises water.

48. The composite of claim 38, wherein the superabsorbent-containing composite has a complex fluid retention capacity of between 0 and about 20 g/g.

49. The composite of claim 38, wherein the superabsorbent-containing composite has a complex fluid retention capacity of at least about 13 g/g.

50. The composite of claim 38, wherein the coating material is capable of selectively removing at least a portion of an amount of at least one other specific component of the complex fluid.

* * * * *